United States Patent
Palese et al.

(10) Patent No.: US 10,278,689 B2
(45) Date of Patent: May 7, 2019

(54) SUTURE PASSER WITH TISSUE REINFORCEMENT POSITIONER

(71) Applicant: Biomet Manufacturing, LLC, Warsaw, IN (US)

(72) Inventors: Christopher Palese, South Whitley, IN (US); Kevin T. Stone, Winona Lake, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 548 days.

(21) Appl. No.: 14/137,277

(22) Filed: Dec. 20, 2013

(65) Prior Publication Data

US 2015/0173742 A1 Jun. 25, 2015

(51) Int. Cl.
*A61B 17/00* (2006.01)
*A61B 17/04* (2006.01)
(Continued)

(52) U.S. Cl.
CPC ...... *A61B 17/0469* (2013.01); *A61B 17/0401* (2013.01); *A61B 17/0482* (2013.01);
(Continued)

(58) Field of Classification Search
CPC ............ A61B 17/0469; A61B 17/0401; A61B 17/0482; A61B 17/062; A61B 2017/0046; A61B 2017/0495; A61B 2017/06042; A61B 2017/044; A61B 2017/00477; A61B 2017/0406; A61B 2017/06095; A61B 2017/0409; Y10T 29/49815
See application file for complete search history.

(56) References Cited

U.S. PATENT DOCUMENTS

| 1,822,330 A | 1/1930 | Ainslie |
| 3,349,772 A | 10/1967 | Rygg |

(Continued)

FOREIGN PATENT DOCUMENTS

| DE | 4235602 A1 | 4/1994 |
| EP | 0778004 A1 | 6/1997 |
| WO | WO-9843545 A1 | 10/1998 |

OTHER PUBLICATIONS

"U.S. Appl. No. 14/137,312, Final Office Action dated Feb. 26, 2016", 11 pgs.

(Continued)

*Primary Examiner* — Jocelin C Tanner
(74) *Attorney, Agent, or Firm* — Schwegman Lundberg & Woessner, P.A.

(57) ABSTRACT

The present disclosure describes a suture passer device that includes a handle, a shaft extending from the handle, and a suturing head extending from the shaft and configured to engage tissue. According to one aspect of the present disclosure, the suture passer device includes a tissue reinforcement member holder configured to retain a tissue reinforcement member relative to the suturing head. According to another aspect of the present disclosure, the suture passer device includes a suture carrier secured to the handle and extending through the shaft, and the suturing head includes a first jaw and a second jaw. Methods of using a suture passer device to pass a suture through tissue and to attach soft tissue to bone are also described.

12 Claims, 17 Drawing Sheets

(51) Int. Cl.
*A61B 17/06* (2006.01)
*A61B 17/062* (2006.01)

(52) U.S. Cl.
CPC ..... *A61B 17/062* (2013.01); *A61B 2017/0046* (2013.01); *A61B 2017/00477* (2013.01); *A61B 2017/044* (2013.01); *A61B 2017/0406* (2013.01); *A61B 2017/0409* (2013.01); *A61B 2017/0495* (2013.01); *A61B 2017/06042* (2013.01); *A61B 2017/06095* (2013.01); *Y10T 29/49815* (2015.01)

(56) References Cited

U.S. PATENT DOCUMENTS

| | | |
|---|---|---|
| 3,842,840 A | 10/1974 | Schweizer |
| 3,946,740 A | 3/1976 | Bassett |
| 3,946,840 A | 3/1976 | Sommer |
| 4,161,951 A | 7/1979 | Scanlan, Jr. |
| 4,164,225 A | 8/1979 | Johnson et al. |
| 4,890,615 A | 1/1990 | Caspari et al. |
| 4,923,461 A | 5/1990 | Caspari et al. |
| 4,926,860 A | 5/1990 | Stice et al. |
| 4,957,398 A | 9/1990 | Schneider et al. |
| 4,957,498 A | 9/1990 | Caspari et al. |
| 5,188,636 A | 2/1993 | Fedotov |
| 5,222,962 A | 6/1993 | Burkhart |
| 5,250,054 A | 10/1993 | Li |
| 5,254,126 A | 10/1993 | Filipi et al. |
| 5,318,577 A | 6/1994 | Li |
| 5,397,325 A | 3/1995 | Della Badia et al. |
| 5,454,827 A | 10/1995 | Aust et al. |
| 5,474,565 A | 12/1995 | Trott |
| 5,522,820 A * | 6/1996 | Caspari ............... A61B 17/0625 606/139 |
| 5,573,542 A | 11/1996 | Stevens |
| 5,618,290 A | 4/1997 | Toy et al. |
| 5,618,294 A | 4/1997 | Aust et al. |
| 5,702,407 A | 12/1997 | Kaji |
| 5,713,908 A | 2/1998 | Jameel et al. |
| 5,730,747 A | 3/1998 | Ek et al. |
| 5,741,278 A | 4/1998 | Stevens et al. |
| 5,820,628 A | 10/1998 | Middleman et al. |
| 5,824,009 A | 10/1998 | Fukuda et al. |
| 5,851,212 A | 12/1998 | Zirps et al. |
| 5,868,760 A | 2/1999 | McGuckin, Jr. |
| 5,885,288 A | 3/1999 | Aust et al. |
| 5,899,914 A | 5/1999 | Zirps et al. |
| 5,919,199 A | 7/1999 | Mers Kelly et al. |
| 5,935,149 A | 8/1999 | Ek |
| 5,938,678 A | 8/1999 | Zirps et al. |
| 5,947,982 A | 9/1999 | Duran |
| 5,972,005 A | 10/1999 | Stalker et al. |
| 6,048,339 A | 4/2000 | Zirps et al. |
| 6,051,006 A | 4/2000 | Shluzas et al. |
| 6,053,907 A | 4/2000 | Zirps |
| 6,062,951 A | 5/2000 | Zirps |
| 6,077,277 A | 6/2000 | Mollenauer et al. |
| 6,077,287 A | 6/2000 | Taylor et al. |
| 6,171,316 B1 | 1/2001 | Kovac et al. |
| 6,187,000 B1 | 2/2001 | Davison et al. |
| 6,283,979 B1 | 9/2001 | Mers Kelly et al. |
| 6,524,320 B2 | 2/2003 | DiPoto |
| 6,533,795 B1 | 3/2003 | Tran et al. |
| 6,626,929 B1 | 9/2003 | Bannerman |
| RE38,335 E | 11/2003 | Aust et al. |
| 6,645,218 B1 | 11/2003 | Cassidy et al. |
| 6,652,553 B2 | 11/2003 | Davison et al. |
| 6,743,239 B1 | 6/2004 | Kuehn et al. |
| 6,743,241 B2 | 6/2004 | Kerr |
| 6,755,843 B2 | 6/2004 | Chung et al. |
| 6,896,686 B2 | 5/2005 | Weber |
| 6,984,237 B2 | 1/2006 | Hatch et al. |
| D523,554 S | 6/2006 | Weisel |
| 7,112,208 B2 | 9/2006 | Morris et al. |
| 7,166,116 B2 | 1/2007 | Lizardi et al. |
| 7,377,926 B2 | 5/2008 | Topper et al. |
| 7,381,212 B2 | 6/2008 | Topper et al. |
| 7,572,265 B2 | 8/2009 | Stone et al. |
| 7,585,305 B2 | 9/2009 | Dreyfuss |
| 7,601,165 B2 | 10/2009 | Stone |
| 7,658,751 B2 | 2/2010 | Stone et al. |
| 7,842,050 B2 | 11/2010 | Diduch et al. |
| 7,879,046 B2 | 2/2011 | Weinert et al. |
| 7,879,076 B2 | 2/2011 | Litovitz et al. |
| 7,905,903 B2 | 3/2011 | Stone et al. |
| 8,057,489 B2 | 11/2011 | Stone et al. |
| 8,282,656 B2 | 10/2012 | Hart |
| 8,361,113 B2 | 1/2013 | Stone et al. |
| 9,687,225 B2 | 6/2017 | Palese et al. |
| 2002/0147456 A1 | 10/2002 | Diduch et al. |
| 2003/0065337 A1* | 4/2003 | Topper ............... A61B 17/0469 606/144 |
| 2003/0208187 A1 | 11/2003 | Layer |
| 2003/0208207 A1 | 11/2003 | Layer |
| 2003/0233106 A1 | 12/2003 | Dreyfuss |
| 2004/0181242 A1 | 9/2004 | Stack et al. |
| 2004/0199184 A1 | 10/2004 | Topper et al. |
| 2004/0249394 A1 | 12/2004 | Morris et al. |
| 2004/0260314 A1 | 12/2004 | Lizardi et al. |
| 2005/0234479 A1 | 10/2005 | Hatch et al. |
| 2005/0288690 A1 | 12/2005 | Bourque et al. |
| 2007/0060953 A1 | 3/2007 | Morris et al. |
| 2007/0149986 A1 | 6/2007 | Morris et al. |
| 2008/0208221 A1* | 8/2008 | Murray ............... A61B 17/0469 606/145 |
| 2009/0088781 A1* | 4/2009 | Prestel ............... A61B 17/0469 606/148 |
| 2009/0270886 A1 | 10/2009 | Bellafiore et al. |
| 2009/0306684 A1* | 12/2009 | Stone ............... A61B 17/0469 606/145 |
| 2010/0121352 A1 | 5/2010 | Murray et al. |
| 2010/0137887 A1 | 6/2010 | Crockett et al. |
| 2010/0241142 A1* | 9/2010 | Akyuz ............... A61B 17/0469 606/144 |
| 2011/0060350 A1 | 3/2011 | Powers et al. |
| 2011/0087245 A1 | 4/2011 | Weinert et al. |
| 2011/0098727 A1 | 4/2011 | Kaiser et al. |
| 2011/0118760 A1* | 5/2011 | Gregoire ............ A61B 17/0483 606/145 |
| 2011/0208240 A1 | 8/2011 | Stone et al. |
| 2011/0251626 A1* | 10/2011 | Wyman ............... A61B 17/0469 606/144 |
| 2015/0173743 A1 | 6/2015 | Palese et al. |

OTHER PUBLICATIONS

"U.S. Appl. No. 14/137,312, Non Final Office Action dated Nov. 5, 2015", 17 pgs.
"U.S. Appl. No. 14/137,312, Preliminary Amendment filed Apr. 23, 2015", 10 pgs.
"U.S. Appl. No. 14/137,312, Response filed Feb. 3, 2016 to Non Final Office Action dated Nov. 5, 2015", 11 pgs.
"U.S. Appl. No. 14/137,312, Response filed Oct. 19, 2015 to Restriction Requirement dated Aug. 21, 2015", 8 pgs.
"U.S. Appl. No. 14/137,312, Restriction Requirement dated Aug. 21, 2015", 7 pgs.
"U.S. Appl. No. 14/137,312, Non Final Office Action dated Aug. 12, 2016", 13 pgs.
"U.S. Appl. No. 14/137,312, Response filed May 25, 2016 to Final Office Action dated Feb. 26, 2016", 11 pgs.
"U.S. Appl. No. 14/137,312, Final Office Action dated Dec. 15, 2016", 11 pgs.
"U.S. Appl. No. 14/137,312, Response filed Nov. 14, 2016 to Non Final Office Action dated Aug. 12, 2016", 12 pgs.
"U.S. Appl. No. 14/137,312, Notice of Allowance dated Mar. 7, 2017", 9 pgs.
"U.S. Appl. No. 14/137,312, Response filed Feb. 15, 2017 to Final Office Action dated Dec. 15, 2016", 10 pgs.

(56) References Cited

OTHER PUBLICATIONS

"SportMesh™ Soft Tissue Reinforcement," by Arthrotek®, a Biomet® company of Warsaw, Indiana (2006) 4 sheets.

* cited by examiner

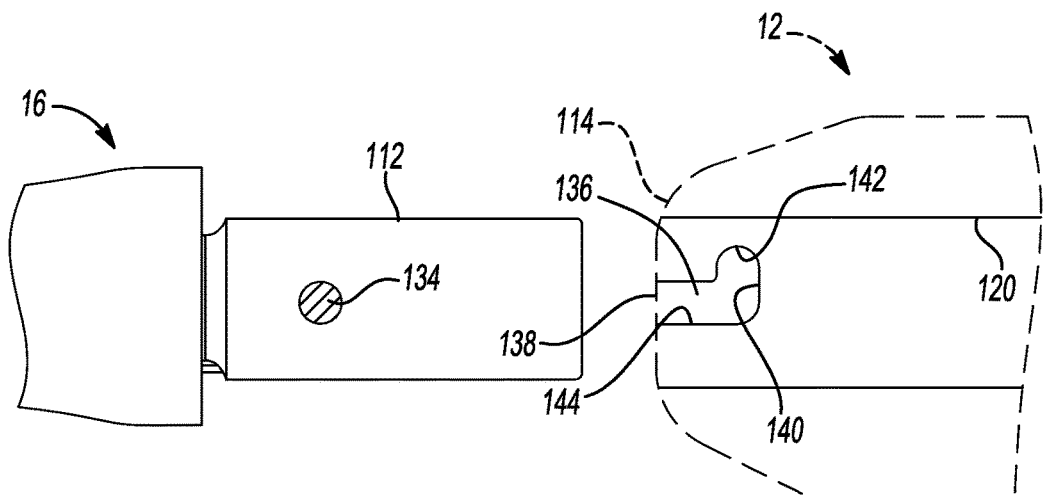
_Fig-9_
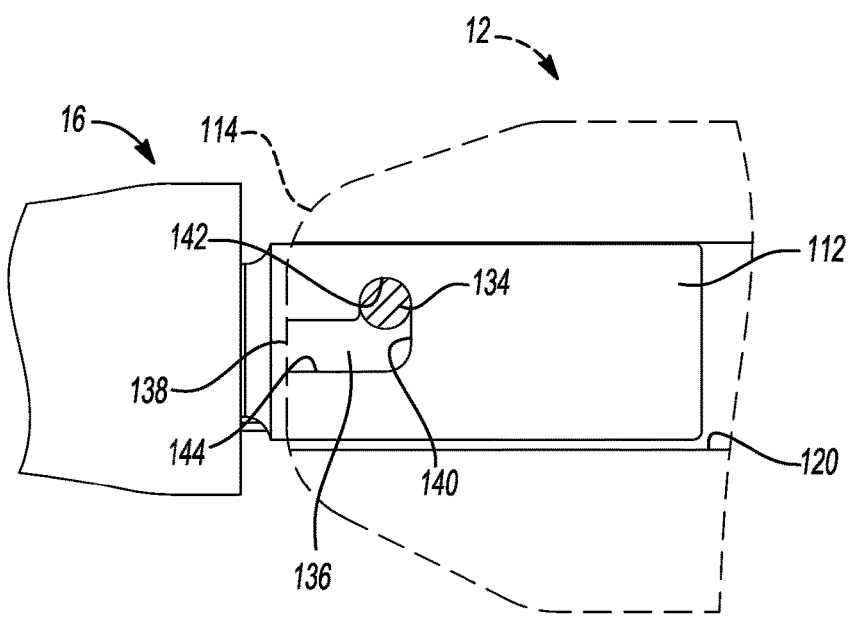
_Fig-10_

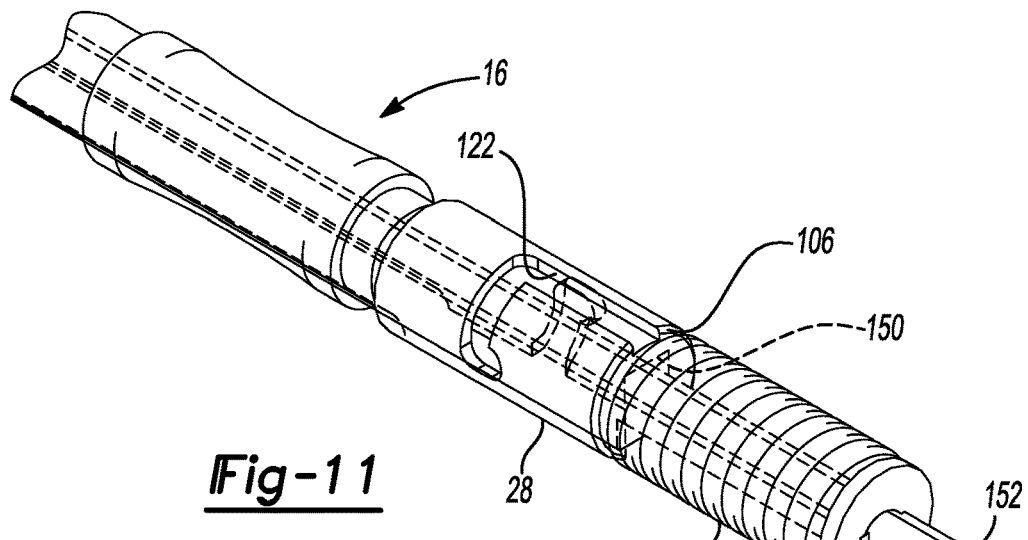
*Fig-11*
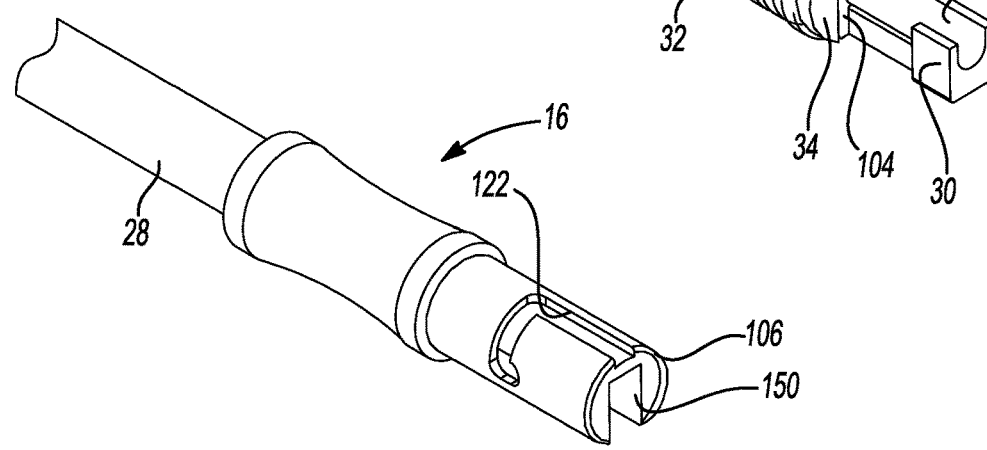
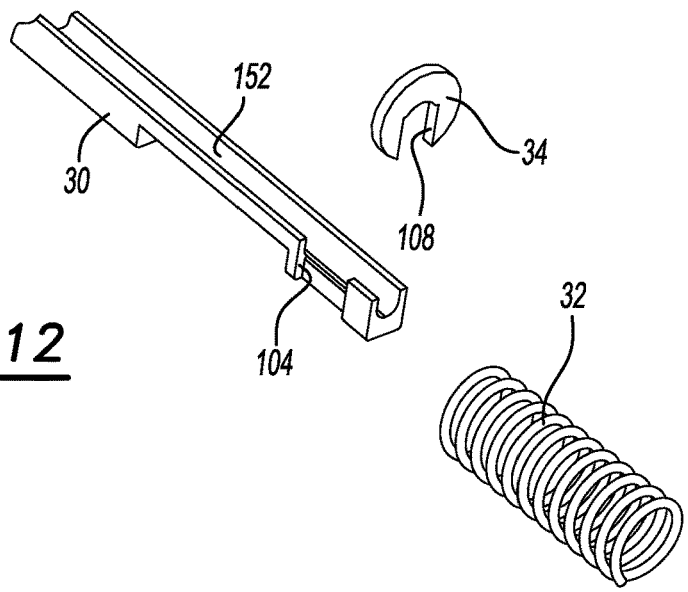
*Fig-12*

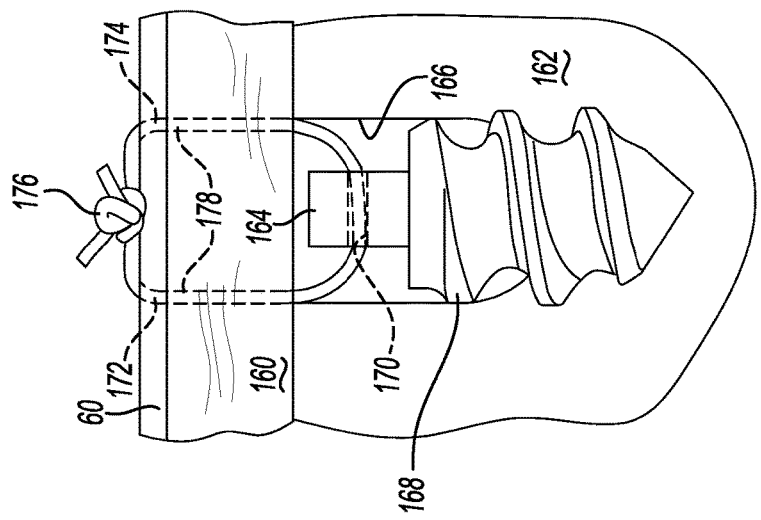
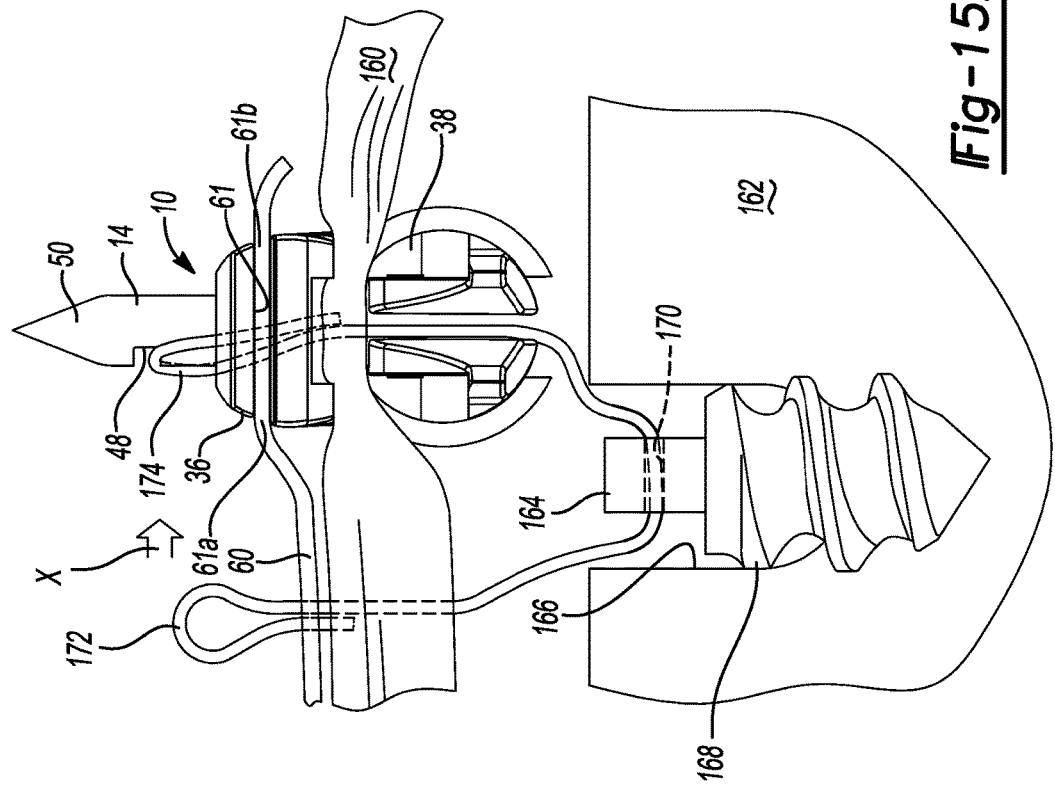

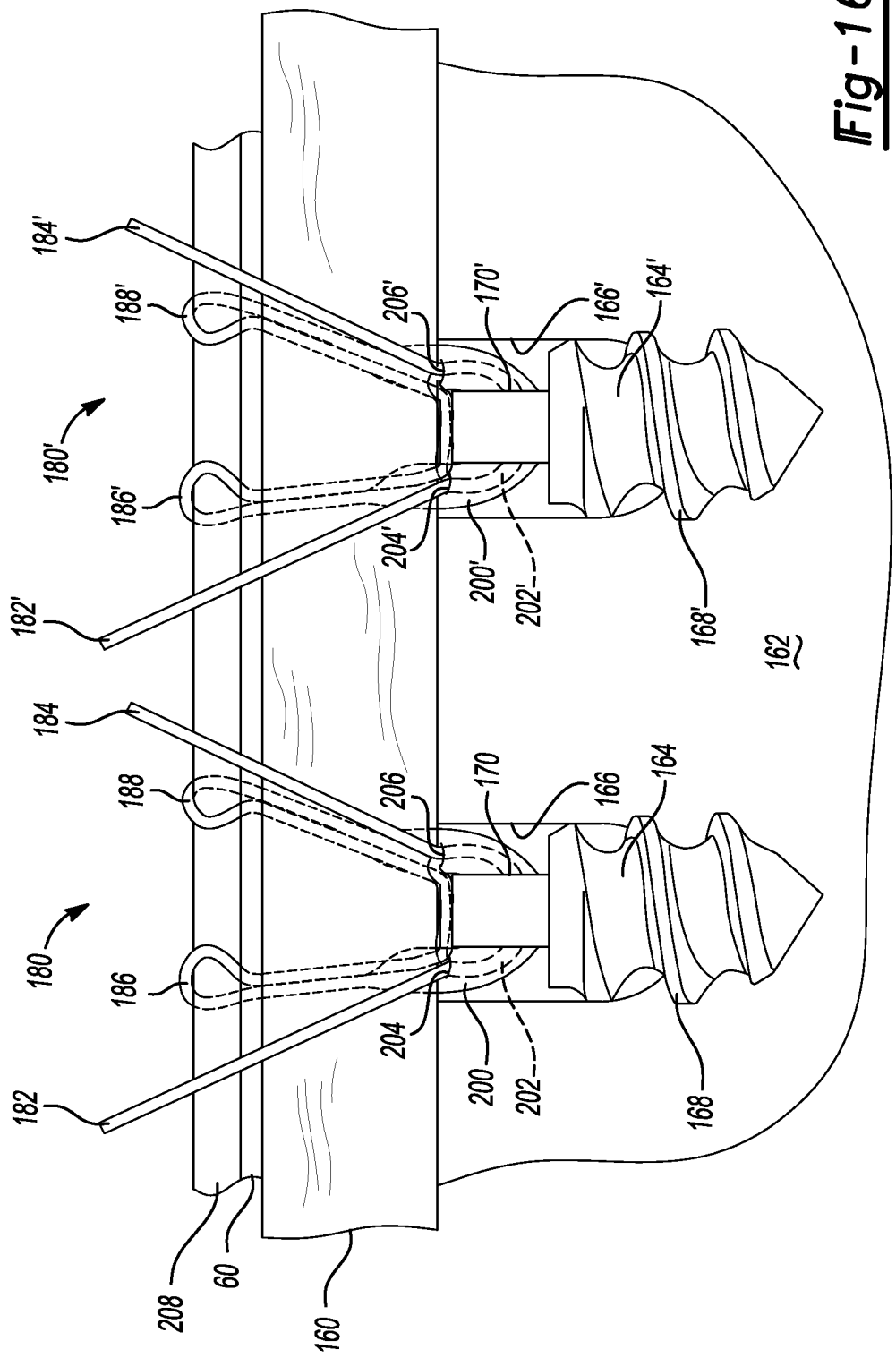

SUTURE PASSER WITH TISSUE REINFORCEMENT POSITIONER

CROSS-REFERENCE TO RELATED APPLICATIONS

The present disclosure is related to U.S. patent application Ser. No. 14/137,312, entitled "Suture Passer with Tissue Reinforcement Positioner", filed Dec. 20, 2013. The entire disclosure of the application referenced above is incorporated herein by reference.

FIELD

The present disclosure relates to a suture passer with tissue reinforcement positioner.

BACKGROUND

This section provides background information related to the present disclosure which is not necessarily prior art.

Various devices and methods are known for suturing soft tissue in connection with arthroscopic, endoscopic, or other surgical procedures. These and other small-incision or less invasive surgical procedures generally require that suturing and the associated manipulation of suturing are performed in confined areas which are not easily accessible.

Although the existing devices can be satisfactory for their intended purposes, there is still a need for procedures and devices that provide greater control in the passage of sutures, greater control in the passage of delicate sutures, and increased flexibility in the types and thicknesses of tissues that can be sutured in ordinary and in less invasive procedures.

SUMMARY

This section provides a general summary of the disclosure, and is not a comprehensive disclosure of its full scope or all of its features.

The present disclosure describes a suture passer device that includes a handle, a shaft extending from the handle, and a suturing head extending from the shaft and configured to engage tissue. According to one aspect of the present disclosure, the suture passer device includes a tissue reinforcement member holder configured to retain a tissue reinforcement member relative to the suturing head. According to another aspect of the present disclosure, the suture passer device includes a suture carrier secured to the handle and extending through the shaft, and the suturing head includes a first jaw and a second jaw. Methods of using the suture passer device to pass a suture through tissue and to attach soft tissue to bone are also described.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 9 is a side view of an alternative embodiment of the shaft assembly and the handle assembly with a proximal end of the shaft assembly disconnected from a distal end of the handle assembly;

FIG. 10 is a side view of the alternative embodiment of the shaft assembly and the handle assembly with the proximal end of the shaft assembly connected to the distal end of the handle assembly;

FIG. 11 is an isometric view of the proximal end of the shaft assembly with an inner shaft inserted into an outer shaft;

FIG. 12 is an isometric view of a proximal end of a shaft assembly with the inner shaft removed from the outer shaft;

FIG. 15A is an end view of the suturing head passing two portions of a suture through soft tissue and the tissue reinforcement construct, the suture extending through a suture anchor secured in a hole in bone;

FIG. 15B is an end view of the two portions of the suture tied in a knot to form an adjustable loop that secures the soft tissue to the bone;

FIG. 16B is an end view of the locking member extending through the loops and preventing the loops from being pulled through the soft tissue and the tissue reinforcement member as the loops are tightened;

Corresponding reference numerals indicate corresponding parts throughout the several views of the drawings.

DETAILED DESCRIPTION

Figure 1:
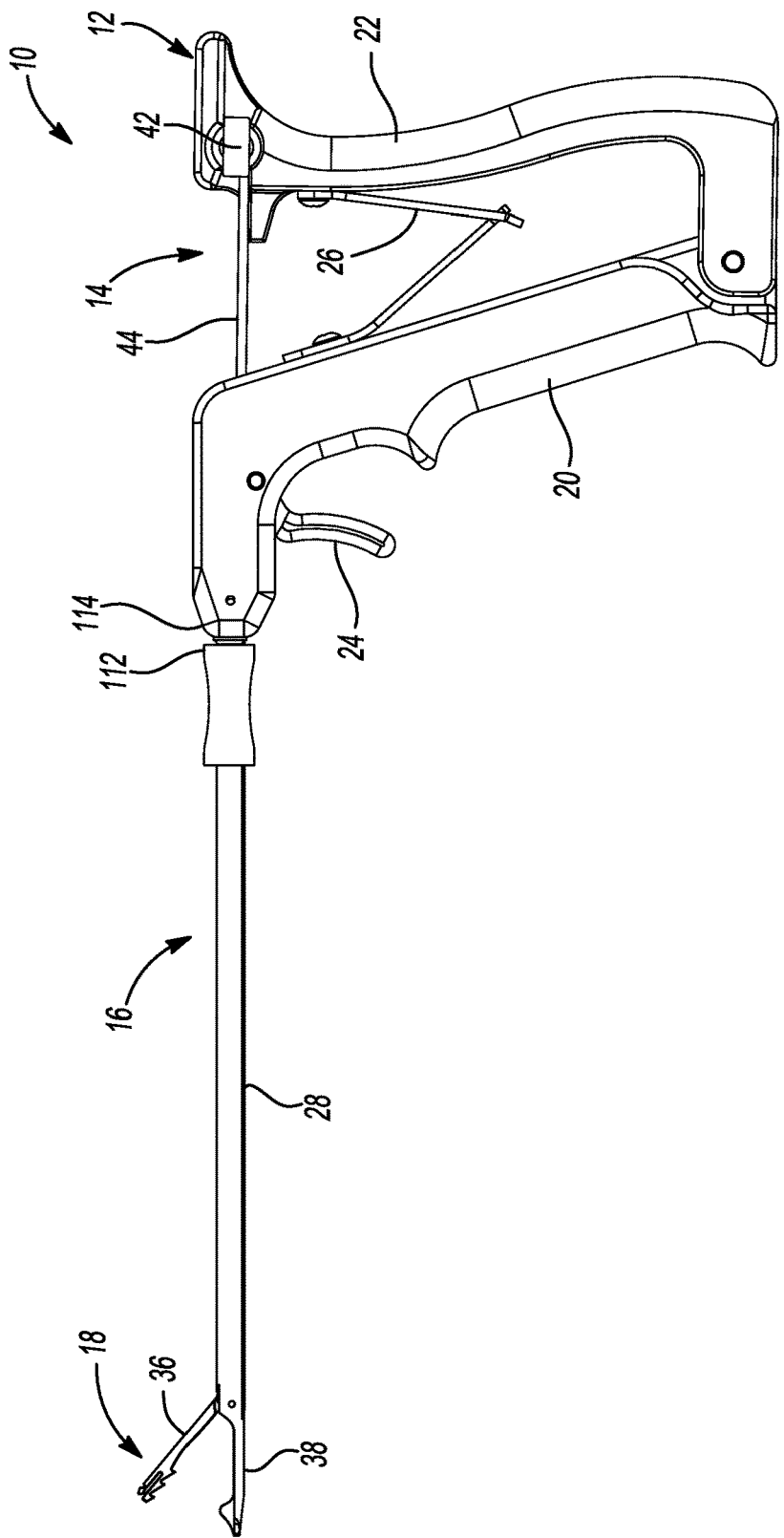
FIG. 1 is a side view of a suture passer device according to the principles of the present disclosure.
Figure 2:
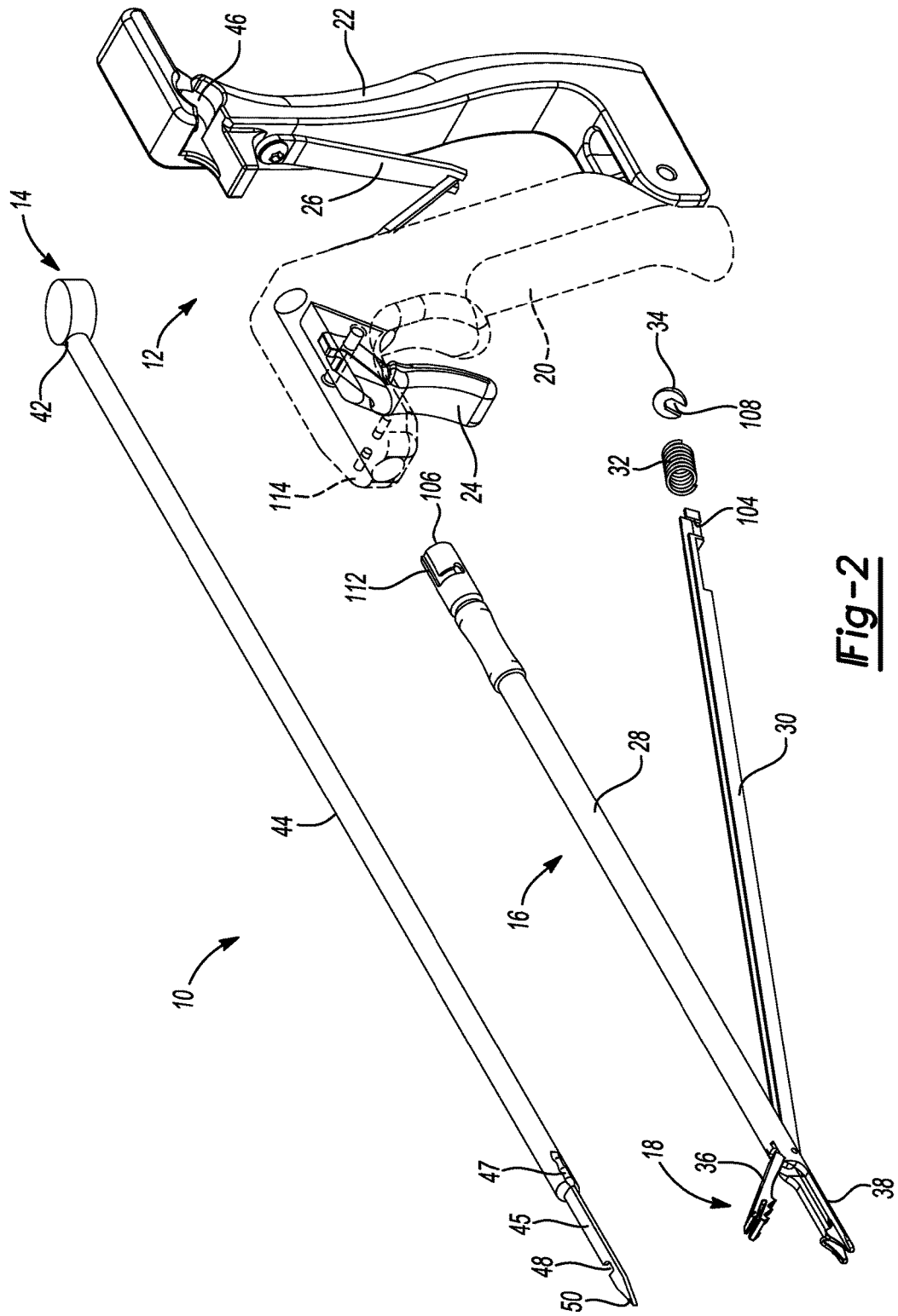
FIG. 2 is an exploded isometric view of the suture passer device shown in FIG. 1.

Example embodiments will now be described more fully with reference to the accompanying drawings.

Referring now to FIGS. 1, 2, 3A, 3B, 4A, and 4B, a suture passer device 10 includes a handle assembly 12, a suture carrier 14, a shaft assembly 16, and a suturing head 18. The handle assembly 12 includes a front handle 20, a rear handle 22, a trigger 24, and a handle spring 26. The shaft assembly 16 includes an outer shaft 28, an inner shaft 30, a shaft spring 32, and a washer 34. The spring 32 and the washer 34 can be welded to the inner shaft 30. The suturing head 18 includes an upper jaw 36 and a lower jaw 38. The handle assembly 12 is operable to actuate the upper jaw 36 of the suturing head 18 from an open position (FIG. 3) to a closed position (FIG. 4) in order to clamp or engage soft tissue between the upper and lower jaws 36, 38. The handle assembly 12 is also operable to actuate the suture carrier 14 from a retracted position (FIG. 3) to an extended position (FIG. 4) to pass a suture 40 through soft tissue that is clamped or held between the upper and lower jaws 36, 38.

The suture carrier 14 includes a proximal body 42 having a round plinth, disk, or hockey puck shape, a cylindrical body 44, and a flat, elongate body 45. The proximal body 42 is disposed at the proximal end of the suture carrier 14 and is configured to be retained within a pocket 46 in the rear handle 22. The cylindrical body 44 is attached to the proximal body 42 and extends from the proximal body 42 to the elongate body 45. The elongate body 45 is attached to the cylindrical body 44 using, for example, a weld 47, and extends from the cylindrical body 44 to the distal end of the suture carrier 14. The elongate body 45 has a notch 48 adjacent to its distal end for holding the suture 40 and a pointed tip 50 at its distal end for piercing a hole in soft tissue so that the suture carrier 14 and the suture 40 can be passed through the tissue. The proximal body 42 can be made from plastic, and the cylindrical and elongate bodies 44, 45 can be made from a flexible material such as Nitinol or a flexible polymer.

With particular reference to FIGS. 3A, 3B, 4A, and 4B, the upper jaw 36 of the suturing head 18 includes teeth 52, a tissue reinforcement member holder 54, a suture carrier receptacle 56, and a suture retaining mechanism 58. The teeth 52 are configured to bite into or grip soft tissue when the upper jaw 36 is in the closed position. The tissue reinforcement member holder 54 is configured to position a tissue reinforcement member 60 (FIGS. 13 and 14) so that the suture carrier 14 and the suture 40 pass through the tissue reinforcement member 60 after passing through soft tissue held between the upper and lower jaws 36, 38. In various implementations, the tissue reinforcement member holder 54 can also or alternatively be included in the lower jaw 38.

The tissue reinforcement member holder 54 can be a slot 61 having open lateral sides 61a, 61b, an open distal end 61c, and a closed proximal end 61d. The tissue reinforcement member 60 can be inserted into the slot 61. In turn, the slot 61 can hold the tissue reinforcement member 60 while allowing the tissue reinforcement member 60 to be slidably adjustable in a lateral direction through the open sides 61a, 61b.

The tissue reinforcement member 60 can be made from a flexible material such as woven, knitted, or braided polyester tape or a non-woven or non-braided material (such as felt), collagen fiber, or other reinforcement member. The tissue reinforcement member 60 is configured to increase the strength of a repair by reinforcing soft tissue. For example, a portion of the suture 40 may be passed through soft tissue and tied in a knot, and the tissue reinforcement member 60 may increase the force required to pull the knot through the soft tissue. The tissue reinforcement member 60 can be one of the example locking members described in U.S. Pat. Pub. No. 2011/0208240 (see, e.g., FIGS. 4 through 9), the disclosure of which is incorporated herein by reference in its entirety. The tissue reinforcement member 60 can be a mesh such as a SportMesh™ Soft Tissue Reinforcement, available from Arthrotek®, a Biomet® company of Warsaw, Ind.

The suture carrier receptacle 56 can be an opening in the upper jaw 36. The suture carrier receptacle 56 can extend through portions of the upper jaw 36 disposed above and below the slot 61. The suture carrier 14 and the suture 40 can be passed through the suture carrier receptacle 56 after passing through soft tissue held between the upper and lower jaws 36, 38.

The suture retaining mechanism 58 prevents unintentional movement of the suture 40 out of the upper jaw 36 by maintaining the suture 40 at or near the suturing head 18. In one embodiment, the suture retaining mechanism 58 can be a flap 62 that fits over the suture carrier receptacle 56. The flap 62 can be made of a resilient and flexible material, such as spring steel, Nitinol, or a flexible polymer. The suture carrier 14 can be passed into the receptacle 56, temporarily disrupting a suture engaging portion 64 of the flap 62 from a closed position in contact with the upper jaw 36 to an open position spaced apart from the upper jaw 36. In turn, the flap 62 can pull the suture 40 through soft tissue held between the upper and lower jaws 36, 38. The suture carrier 14 can then be retracted through the suture carrier receptacle 56, allowing the suture engaging portion 64 to return to the closed position. In turn, the flap 62 biases the suture 40 against the receptacle 56 to prevent the suture 40 from being pulled back through the receptacle 56.

The upper jaw 36 can be rotatably or pivotally coupled to the outer shaft 28 of the shaft assembly 16 using a pin 80, and the lower jaw 38 of the suturing head 18 can be integrally formed with the outer shaft 28. The shaft assembly 16 and the suturing head 18 can be made from metal. The lower jaw 38 can include a suture carrier channel 82 and a suture receptacle 84. The suture carrier channel 82 can guide the suture carrier 14 as the suture carrier 14 is advanced and retracted through the lower jaw 38. The suture carrier channel 82 includes a ramped portion 86 that directs the suture carrier 14 through the suture carrier receptacle 56 in the upper jaw 36. The suture receptacle 84 can be an opening or slot formed into the lower jaw 38. The suture 40 can be passed through the receptacle 84 before being received in the notch 48 in the suture carrier 14.

Figure 3A:
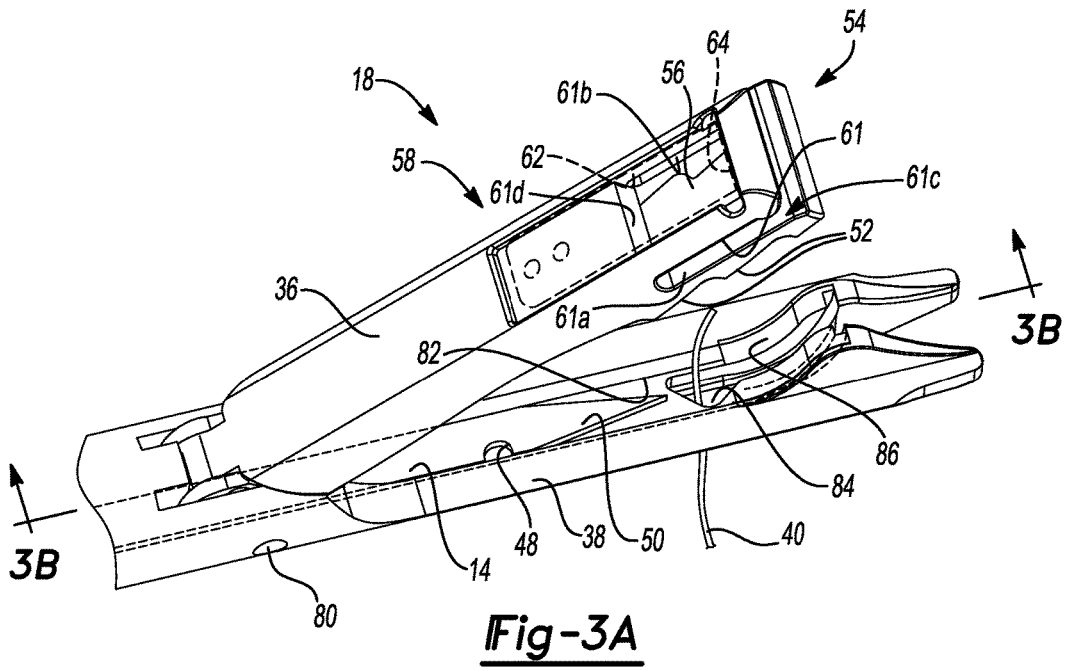
FIG. 3A is an isometric view of a suturing head of the suture passer device with an upper jaw in an open position and a suture carrier in a retracted position.
Figure 3B:
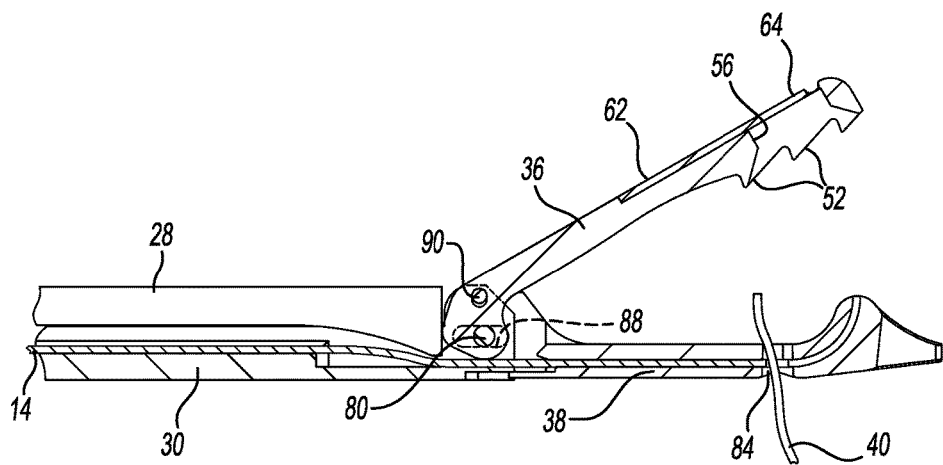
FIG. 3B is a section view taken along line 3B shown in FIG. 3A.
Figure 4A:
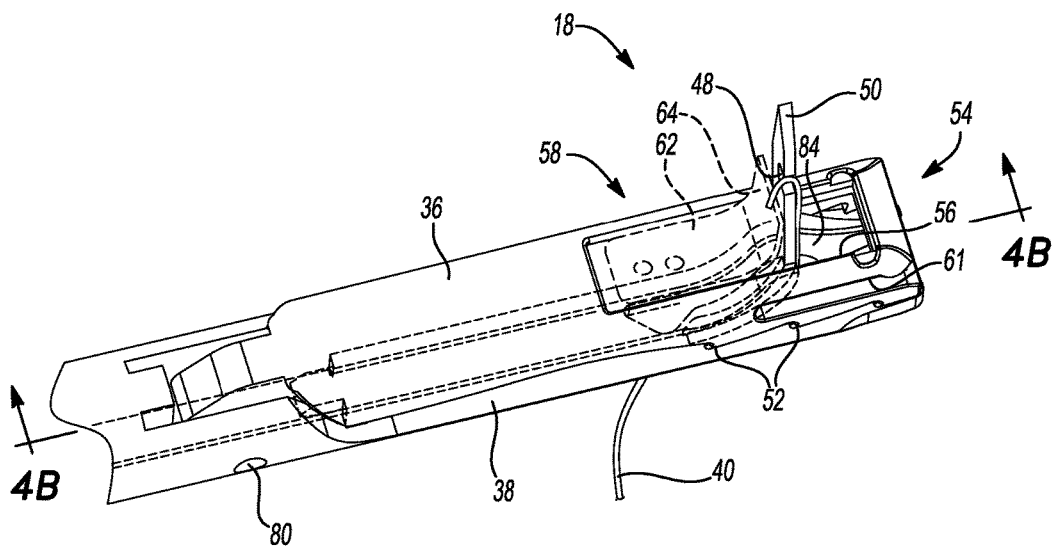
FIG. 4A is an isometric view of the suturing head with the upper jaw in a closed position and the suture carrier in an extended position.
Figure 4B:
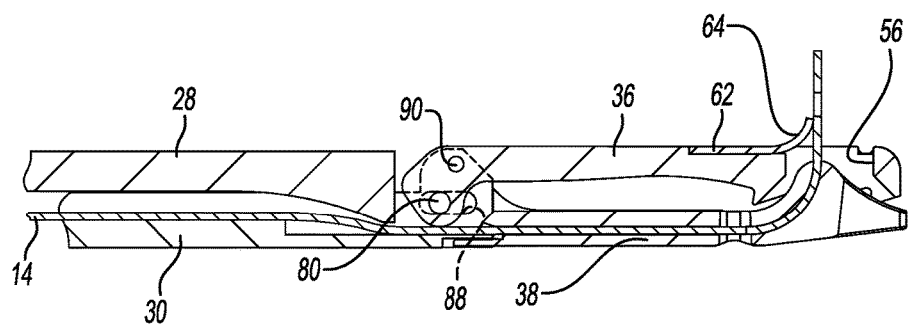
FIG. 4B is a section view taken along line 4B shown in FIG. 4A.

With particular reference to FIGS. 3B and 4B, the inner shaft 30 can also be rotatably or pivotally coupled to the outer shaft 28 using the pin 80. The inner shaft 30 can define an elongate slot 88, and the pin 80 can extend through the slot 88. The slot 88 allows the inner shaft 30 to move distally or proximally relative to the outer shaft 28. The length of the slot 88 can correspond to the amount of longitudinal movement of the inner shaft 30 required to actuate the upper jaw 36 between the open position and the closed position.

The upper jaw 36 can be rotatably or pivotally coupled to the inner shaft 30 using a pin 90. Thus, as the inner shaft 30 axially moves distally relative to the outer shaft 28, the upper jaw 36 rotates or pivots from the open position to the closed position. In this regard, the connections at the pins 80, 90 convert linear movement of the inner shaft 30 into rotational movement of the upper jaw 36.

Figure 5:
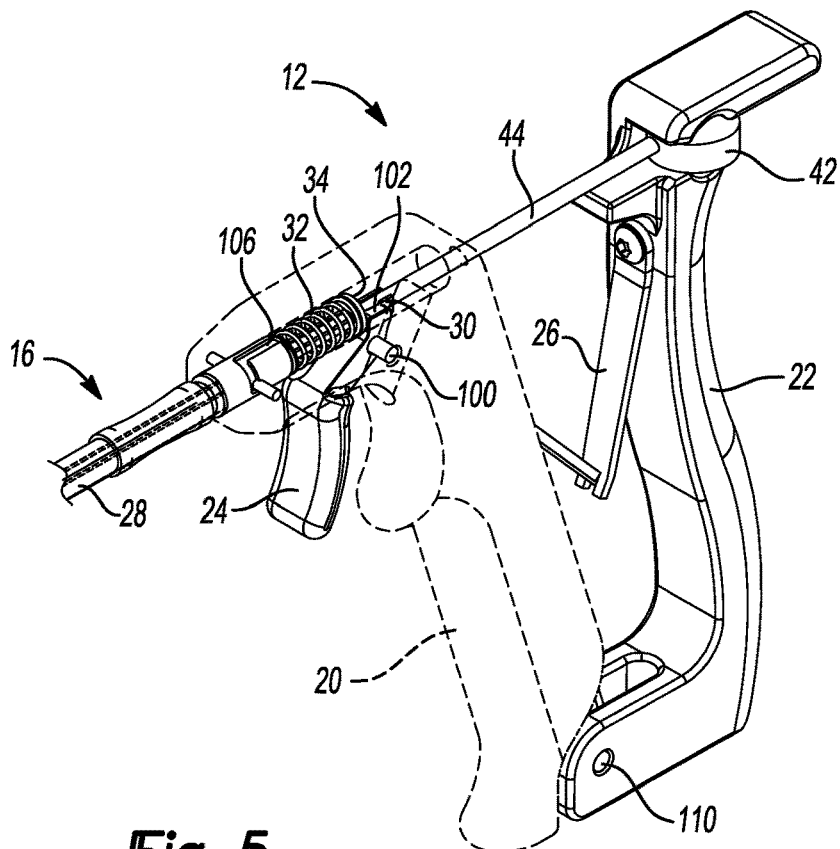
FIG. 5 is an isometric view of a handle assembly of the suture passer device with a trigger and a rear handle in released positions.
Figure 6:
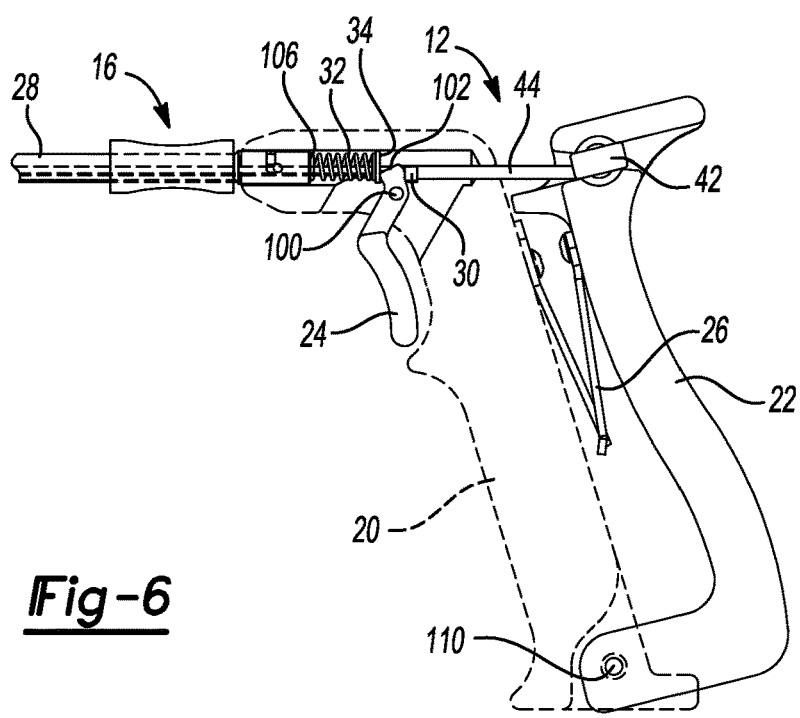
FIG. 6 is a side view of the handle assembly with the trigger and the rear handle in applied positions.

Referring now to FIGS. 5 and 6, the trigger 24 of the handle assembly 12 can be actuated from a released position (FIG. 5) to an applied position (FIG. 6) in order to actuate the upper jaw 36 from the open position to the closed position. In this regard, the trigger 24 can be rotatably or pivotally coupled to the front handle 20 using a pin 100, and the trigger 24 can include a hammer portion 102 that is received within a slot 104 (FIG. 2) in the inner shaft 30. As the trigger 24 is actuated from the released position to the applied position, the hammer portion 102 pushes the inner shaft 30 distally relative to the outer shaft 28. Then, as discussed above, the distal movement of the inner shaft 30 causes the upper jaw 36 to rotate or pivot from the open position to the closed position.

The shaft spring 32 can be captured between a proximal end 106 of the outer shaft 28 and the washer 34. The washer 34 can define a slot 108 (FIG. 2) configured to receive the inner shaft 30. The width of the slot 108 can be less than the width of the inner shaft 30 to yield a press fit between the washer 34 and the inner shaft 30 that fixes the washer 34 onto the inner shaft 30. Thus, when the trigger 24 is released, the biasing force of the shaft spring 32 acting on the washer 34 axially moves the inner shaft 30 proximally. Since the hammer portion 102 of the trigger 24 is received within the slot 104 in the inner shaft 30, the proximal movement of the inner shaft 30 moves the hammer portion 102 proximally and returns the trigger 24 to the released position.

The rear handle 22 can be actuated from a released position (FIG. 5) to an applied position (FIG. 6) in order to actuate the suture carrier 14 from the retracted position to the extended position. In this regard, the rear handle 22 can be rotatably or pivotally coupled to the front handle 20 using a pin 110, and the handle spring 26 can bias the rear handle 22 toward the released position. As the rear handle 22 is actuated from the released position to the applied position, the engagement between the proximal body 42 of the suture carrier 14 and the rear handle 22 moves the suture carrier 14 from the retracted position to the extended position.

The handle spring 26 can be a leaf spring and the shaft spring 32 can be a coil spring, as shown. Alternatively, both the handle spring 26 and the shaft spring 32 can be coil springs. In various embodiments, the spring rate of the handle spring 26 is less than the spring rate of the shaft spring 32. Thus, if the rear handle 22 and the trigger 24 are applied at the same time, the upper jaw 36 rotates or pivots to the closed position before the suture carrier 14 advances to the extended position. This facilitates clamping soft tissue between the upper and lower jaws 36, 38 before passing the suture carrier 14 and the suture 40 through the soft tissue.

Referring again to FIGS. 1 and 2, a proximal end 112 of the shaft assembly 16 can be easily disconnected from a distal end 114 of the handle assembly 12, and the outer shaft 28 can be rotated or pivoted away from the inner shaft 30. This facilitates cleaning, disinfecting, and sterilizing the suture passer device 10. In various implementations, the front handle 20, the rear handle 22, and the trigger 24 can be made from plastic. In these implementations, after a surgery, the shaft assembly 16 can be disconnected from the handle assembly 12, and the handle assembly 12 can be discarded.

Figure 7:
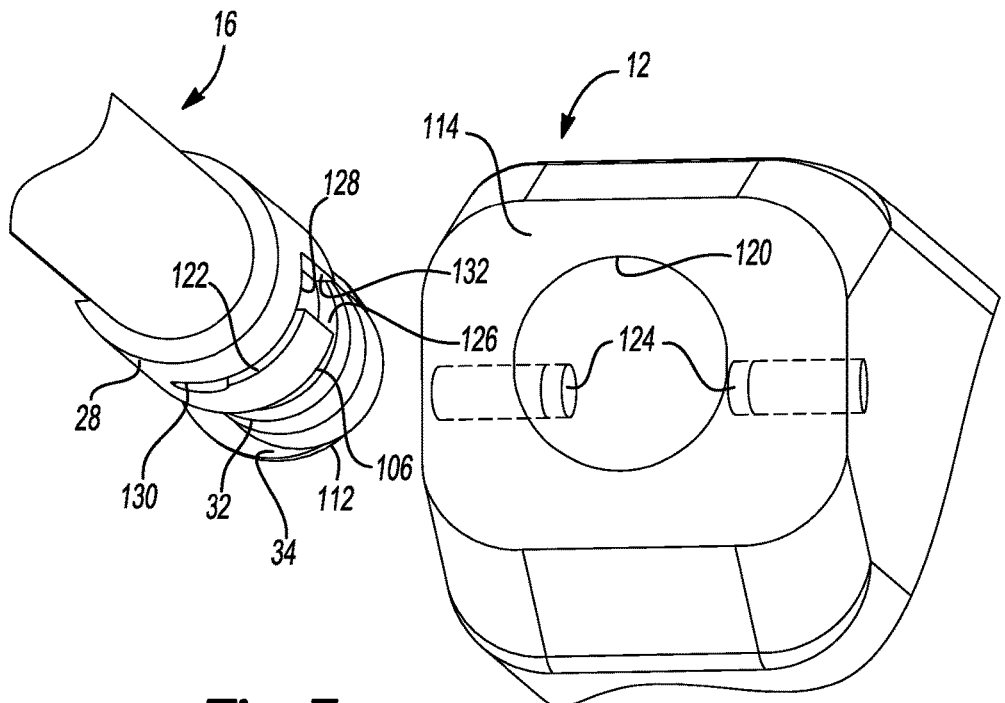
FIG. 7 is an isometric view of a proximal end of a shaft assembly of the suture passer device disconnected from a distal end of the handle assembly.
Figure 8:
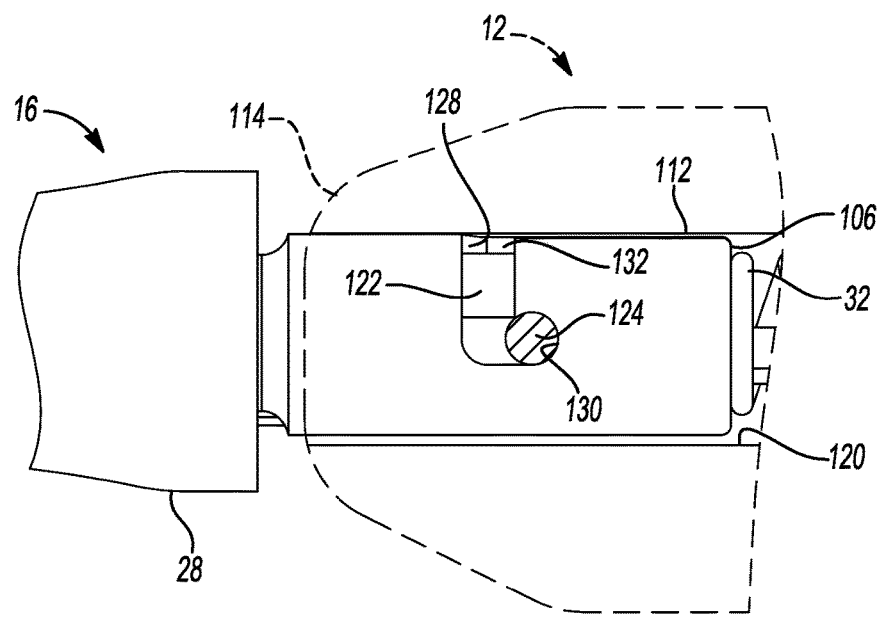
FIG. 8 is a side view of the proximal end of the shaft assembly connected to the distal end of the handle assembly.

Referring now to FIGS. 7 and 8, the proximal end 112 of the shaft assembly 16 can be inserted into a cylindrical channel 120 in the front handle 20 and releasably connected to the handle assembly 12 using a quick-connect mechanism such as a bayonet mount. In this regard, the outer shaft 28 can define a pair of J-shaped slots 122 (only one shown) disposed on opposite sides of the outer shaft 28, and the front handle 20 can include pins 124 extending into the cylindrical channel 120. To connect the shaft assembly 16 to the handle assembly 12, the open ends 126 of the J-shaped slots 122 can be aligned with the pins 124. The proximal end 112 of the shaft assembly 16 can then be inserted into the cylindrical channel 120 until the pins 124 contact radial surfaces 128 of the J-shaped slots 122. The shaft assembly 16 can then be rotated relative to the handle assembly 12 until the pins 124 contact closed ends 130 of the J-shaped slots 122.

As discussed above, the shaft spring 32 may be captured between the proximal end 106 of the outer shaft 28 and the washer 34. The biasing force of the shaft spring 32 may urge the outer shaft 28 distally, thereby engaging the pins 124 with the closed ends 130 of the J-shaped slots 122. Thus, to disconnect the shaft assembly 16 from the handle assembly 12, the outer shaft 28 can be moved by hand further into the cylindrical channel 120 to overcome the biasing force of the shaft spring 32 and disengage the pins 124 from the closed ends 130 of the J-shaped slots 122. The shaft assembly 16 can then be rotated relative to the handle assembly 12 until the pins 124 contact longitudinal surfaces 132 of the J-shaped slots 122. The proximal end 112 of the shaft assembly 16 can then be withdrawn from the cylindrical channel 120.

Referring to FIGS. 9 and 10, an alternative embodiment of a releasable connection between the shaft assembly 16 and the handle assembly 12 is illustrated. In this embodiment, the proximal end 112 of the shaft assembly 16 includes pins 134 (only one shown) disposed on opposite sides thereof, and the distal end 114 of the handle assembly 12 defines L-shaped slots 136. To connect the shaft assembly 16 to the handle assembly 12, the pins 134 are aligned with open ends 138 of the L-shaped slots 136. The proximal end 112 of the shaft assembly 16 can then be inserted into the cylindrical channel 120 until the pins 134 contact radial surfaces 140 of the L-shaped slots 136. The shaft assembly 16 can then be rotated relative to the handle assembly 12 until the pins 134 contact closed ends 142 of the L-shaped slots 136. Although not shown in FIGS. 9 and 10, the shaft spring 32 may bias the outer shaft 28 distally, thereby maintaining the engagement between the pins 134 and the closed ends 142 of the L-shaped slots 136.

To disconnect the shaft assembly 16 from the handle assembly 12, the shaft assembly 16 can be rotated relative to the handle assembly 12 until the pins 134 contact longitudinal surfaces 144 of the L-shaped slots 136. The proximal end 112 of the shaft assembly 16 can then be withdrawn from the cylindrical channel 120 in the front handle 20. Although not shown in FIGS. 9 and 10, the shaft spring 32 may bias the outer shaft 28 distally, thereby forcing the proximal end 112 of the shaft assembly 16 out of the cylindrical channel 120 in the front handle 20.

Referring now to FIGS. 11 and 12, the proximal end 112 of the shaft assembly 16 is illustrated with the inner shaft 30 inserted into the outer shaft 28 (FIG. 11) and the inner shaft 30 rotated or pivoted away from the outer shaft 28 (FIG. 12). The embodiment shown in FIGS. 11 and 12 is the same embodiment that is shown in FIGS. 7 and 8 with the J-shaped slots 122 defined in the outer shaft 28 near the proximal end 112 of the shaft assembly 16. The outer shaft 28 can also define a U-shaped channel 150 that is configured to receive the inner shaft 30. The inner shaft 30 can also define a U-shaped channel 152. When the inner shaft 30 is inserted into the U-shaped channel 150 in the outer shaft 28, the U-shaped channels 150, 152 can cooperate to define a fully enclosed channel for guiding the suture carrier 14. The ability to pivot the inner shaft 30 away from the outer shaft 28 exposes interior features, such as the U-shaped channels 150, 152, and makes it easier to disassemble and assemble components of the shaft assembly 16. In turn, the shaft assembly 16 can be easily cleaned, disinfected, and sterilized.

As discussed above, the shaft spring 32 may be captured between the proximal end 106 of the outer shaft 28 and the washer 34. Thus, when the shaft assembly 16 is disconnected from the handle assembly 12, the biasing force of the shaft spring 32 can hold the inner shaft 30 in the U-shaped channel 150 of the outer shaft 28, as shown in FIG. 11. However, the proximal end 106 of the outer shaft 28 may be pulled upward by hand to rotate the outer shaft 28 away from the inner shaft 30. When the outer shaft 28 is rotated away from the inner shaft 30, as shown in FIG. 12, the shaft spring 32 is allowed to relax. Thus, before rotating the outer shaft 28 back toward the inner shaft 30, the shaft spring 32 may be compressed by hand to avoid interference between the shaft spring 32 and the U-shaped channel 150 in the outer shaft 28.

Figure 13:
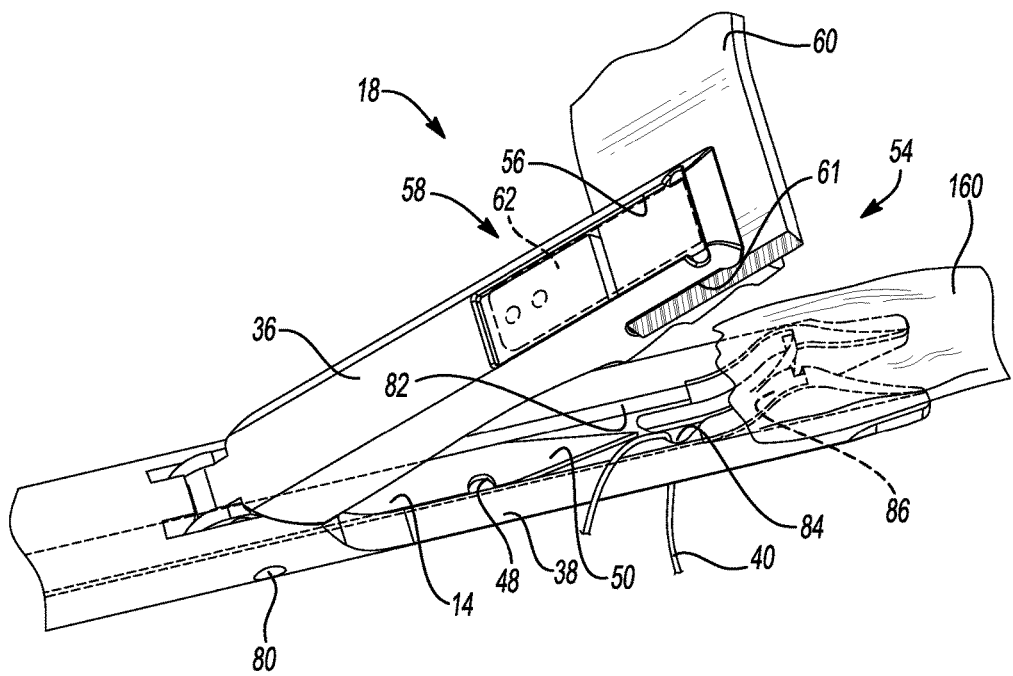
FIG. 13 is an isometric view of the suturing head with the upper jaw in the open position and positioning a tissue reinforcement construct, the suture carrier in the retracted position, a suture extending through a lower jaw, and soft tissue disposed between the lower jaw and the upper jaw.
Figure 14:
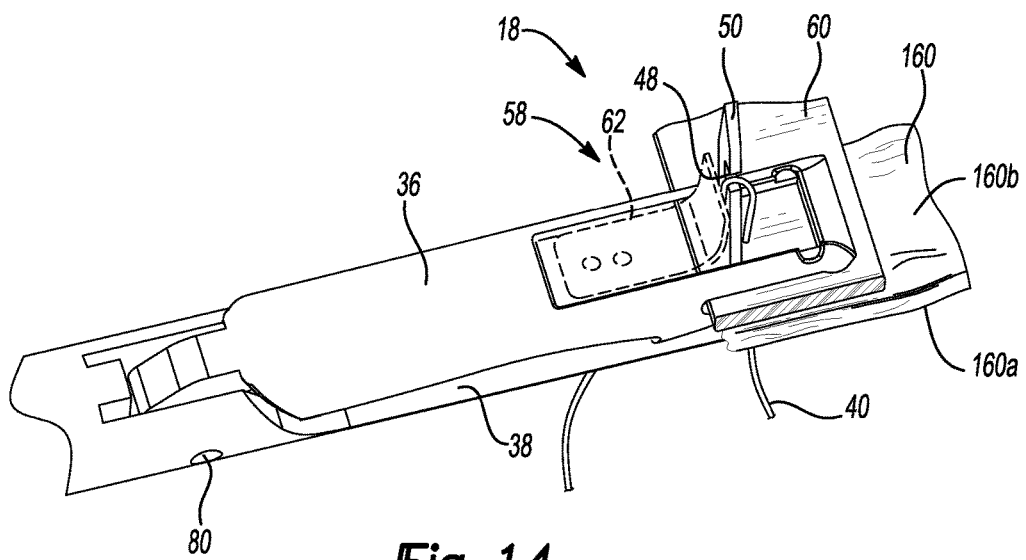
FIG. 14 is an isometric view of the suturing head in the closed position, the soft tissue being held between the upper and lower jaws, and the suture carrier in the extended position and passing a portion of the suture through the soft tissue and the tissue reinforcement construct.

Referring now to FIGS. 13 and 14, the suture passer 10 is illustrated with the tissue reinforcement member 60 positioned or slidably received in the slot 61 in the upper jaw 36, and soft tissue 160 positioned between the upper and lower jaws 36, 38. The slot 61 in the upper jaw 36 of the suture passer 10 can aid in the positioning of the tissue reinforcement member 60 before, during, and after passing the suture 40 through the soft tissue 160. The suture passer 10 can be used to pass the suture 40 through the soft tissue 160 and the tissue reinforcement member 60 substantially simultaneously. For example, using only one hand placed on the handle assembly 12, the suture carrier 14 can be advanced to pass the suture 40 through the soft tissue 160 and the tissue reinforcement member 60 in a single, continuous operation or motion. In addition, using only the suture passer 10, the tissue reinforcement member 60 can be positioned in the path of the suture carrier 14, and the suture carrier 14 can be advanced to pass the suture 40 through the soft tissue 160 and the tissue reinforcement member 60. Thus, a second instrument is not required to hold the tissue reinforcement member 60. Since the suture passer 10 accomplishes the functions of multiple tools while requiring minimal space, the suture passer 10 can be used in an arthroscopic surgery or an open surgery.

In an example method of using the suture passer 10, the reinforcement member 60 is slidably inserted into the slot 61 in the upper jaw 36, and the suture 40 is inserted into the suture receptacle 84 in the lower jaw 38, as shown in FIG. 13. The upper jaw 36 is then closed to clamp and retain the soft tissue 160 between the upper and lower jaws 36, 38 while simultaneously positioning the tissue reinforcement member 60. The suture carrier 14 is then advanced through the suture carrier channel 82 in the lower jaw 38 and the receptacle 56 in the upper jaw 36. As the suture carrier 14 advances through the lower jaw 38, the notch 48 in the suture carrier 14 catches the suture 40. Thus, as the suture carrier 14 advances through the receptacle 56 in the upper jaw 36, the suture carrier 14 passes the suture 40 through both the soft tissue 160 and the tissue reinforcement member 60 substantially simultaneously, as shown in FIG. 14. The suture carrier 14 passes the suture 40 from a first side 160*a* of the soft tissue 160 to a second side 160*b* of the soft tissue 160. As the suture carrier 14 retracts through the receptacle 56 in the upper jaw 36, the suture retention mechanism 58 prevents the suture 40 from retracting with the suture carrier 14 and maintains the suture 40 on the second side 160*b* of the soft tissue 160.

Referring now to FIGS. 15A and 15B, an example method of using the suture passer 10 and the suture 40 to attach the soft tissue 160 to bone 162 is illustrated. First, a suture anchor 164 can be secured within a hole 166 formed in the bone 162. The suture anchor 164 can be a hard, rigid anchor or a soft, deformable anchor. The hole 166 can be preformed or formed by external threads 168 on the anchor 164. The suture 40 can be passed through a hole 170 in the anchor 164 before or after the anchor 164 is secured to the bone 162.

The tissue reinforcement member 60 can then be inserted into the slot 61 in the upper jaw 36 of the suture passer 10, and a first end 172 of the suture 40 can be inserted into the suture receptacle 84 in the lower jaw 38. The upper jaw 36 can then be closed to clamp or retain the soft tissue 160 between the upper and lower jaws 36, 38. The suture carrier 14 can then be advanced to pass the first end 172 of the suture 40 through both the soft tissue 160 and the tissue reinforcement member 60 substantially simultaneously. The suture carrier 14 can then be retracted.

The suture passer 10 can then be moved along the length of tissue reinforcement member 60 in a direction X without removing the member 60 from the slot 61 in the upper jaw 36 since the slot 61 has the open sides 61*a*, 61*b*. The suture passer 10 can then be used to pass a second end 174 of the suture 40 through the soft tissue 160 and the tissue reinforcement member 60. After the first and second ends 172, 174 of the suture 40 are passed through the soft tissue 160 and the tissue reinforcement member 60, the first and second ends 172, 174 can be tied in a slip knot 176 to form an adjustable loop 178. The size of the loop 178 can be decreased to bring the soft tissue 160 closer to the bone 162. The tissue reinforcement member 60 prevents the knot 176 and the suture 40 from being pulled through the soft tissue 160 while the suture 40 is under tension.

Figure 16A:
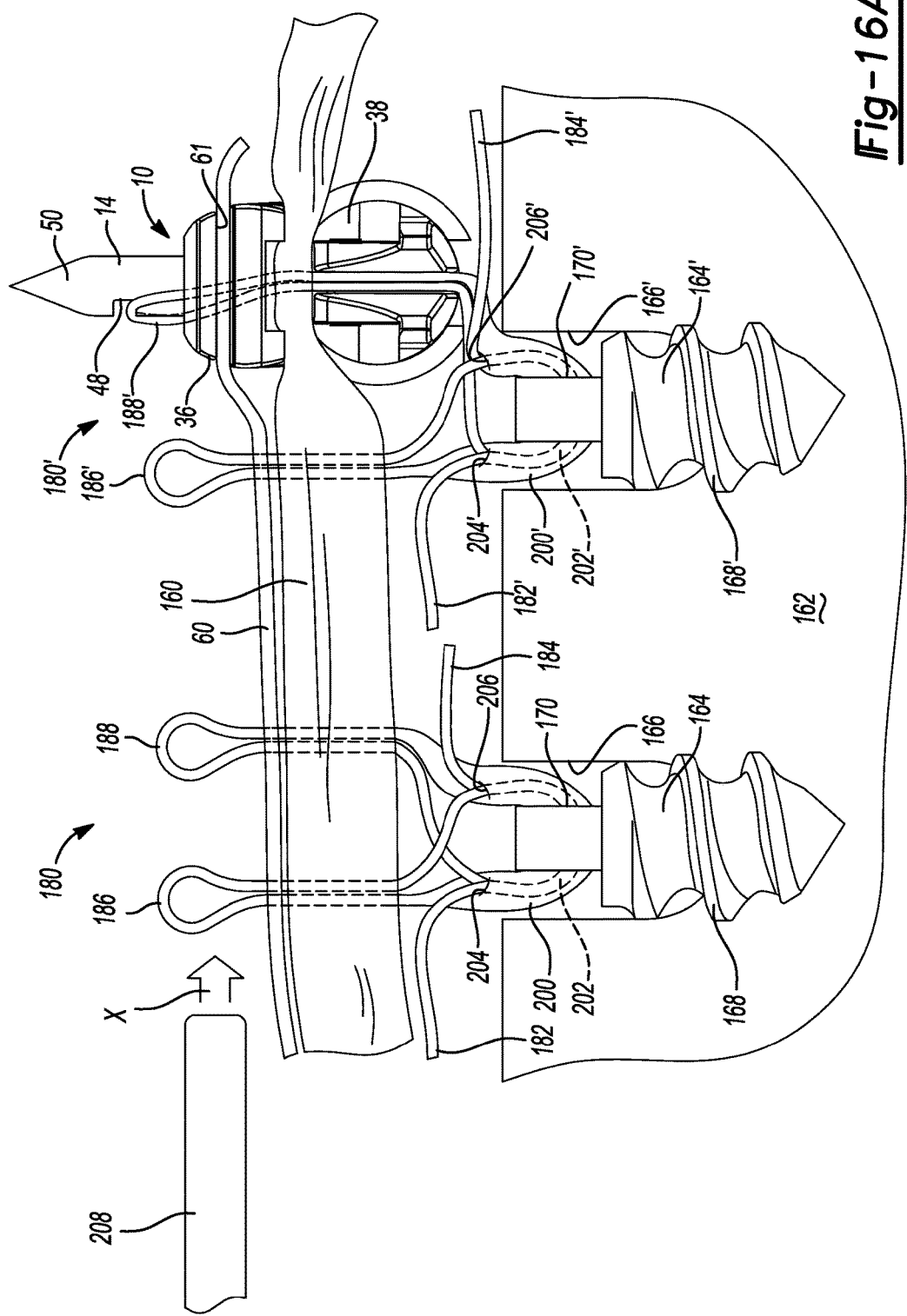
FIG. 16A is an end view of the suturing head passing adjustable loops of a suture construct through soft tissue and the tissue reinforcement construct, the suture construct extending through a suture anchor secured in a hole in bone, and a locking member position adjacent to the loops.

Referring now to FIGS. 16A and 16B, an example method of using the suture passer 10 and a suture construct 180 to attach the soft tissue 160 to bone 162 is illustrated. First, the suture construct 180 can be passed through the hole 170 in the suture anchor 164, and the anchor 164 can be secured within the hole 166 in the bone 162. The suture construct 180 can be formed of a monofilament, a braided fiber or strand, or other flexible material. The suture construct 180 can include a first end 182, a second end 184, a first adjustable loop 186, a second adjustable loop 188, and a braided body 200. The braided body 200 of the suture construct 180 can define a longitudinal passage 202 extending between a first opening 204 and a second opening 206.

The first and second ends 182, 184 and the braided body 200 can be integrally formed as a single braided construct using a braiding process for braiding fibers composed of a biocompatible material. The openings 204, 206 can be created during the braiding process as loose portions between pairs of fibers. The longitudinal passage 202 can be a portion of a longitudinal passage that extends along the entire length of the suture construct 180.

Before forming the adjustable loops 186, 188, the braided body 200 can be positioned within the hole 170 in the anchor 164. The first adjustable loop 186 can then be formed by passing the first end 182 through the longitudinal passage 202 in the direction from the second opening 206 to the first opening 204. Similarly, the second adjustable loop 188 can be formed by passing the second end 184 through the longitudinal passage 202 in the direction from the first opening 204 to the second opening 206.

A second suture anchor 164' can also be secured within a hole 166' in the bone 162, and a suture construct 180' can be passed through a hole 170' in the anchor 164' and arranged to form two adjustable loops 186', 188' as described above. The suture passer 10 can then be used to pass the adjustable loops 186, 188, 186', 188' through the soft tissue 160 and the single, elongated tissue reinforcement member 60 as shown in FIG. 16A. The suture passer 10 can be moved along the length of the tissue reinforcement member 60 in the direction X without removing the member 60 from the slot 61 in the upper jaw 36 since the slot 61 has the open sides 61a, 61b. To this end, the suture passer 10 can be slid axially along the length of the tissue reinforcement member 60 as the member 60 passes through the open sides 61a, 61b of the slot 61.

After the adjustable loops 186, 188, 186', 188' are passed through the soft tissue 160 and the tissue reinforcement member 60, a locking member 208 can be passed through and positioned within the adjustable loops 186, 188, 186', 188'. The locking member 208 can be one of the example locking members described in the U.S. Pat. Pub. No. 2011/0208240 (see, e.g., FIGS. 4 through 9), the disclosure of which is incorporated herein by reference in its entirety. The adjustable loops 186, 188, 186', 188' can be self-locking adjustable loops (e.g., self-locking adjustable loops that have no knots). Examples of self-locking adjustable loops are disclosed in U.S. Pat. Nos. 7,658,751 and 7,601,165, the disclosures of which are incorporated herein by reference in their entirety.

When the locking member 208 is positioned within the adjustable loops 186, 188, 186', 188', the ends 182, 184, 182', 184' can be pulled to decrease the sizes of the adjustable loops 186, 188, 186', 188', respectively, and thereby bring the soft tissue 160 closer to the bone 162. The size of the adjustable loops 186, 188, 186', 188' can be decreased until the soft tissue 160 is in contact with the bone 162 as shown in FIG. 16B. The tissue reinforcement member 60 and the locking member 208 prevent the adjustable loops 186, 188, 186', 188' from being pulled through the soft tissue 160 as the size of the adjustable loops 186, 188, 186', 188' is decreased and after the repair is made.

Figure 17A:
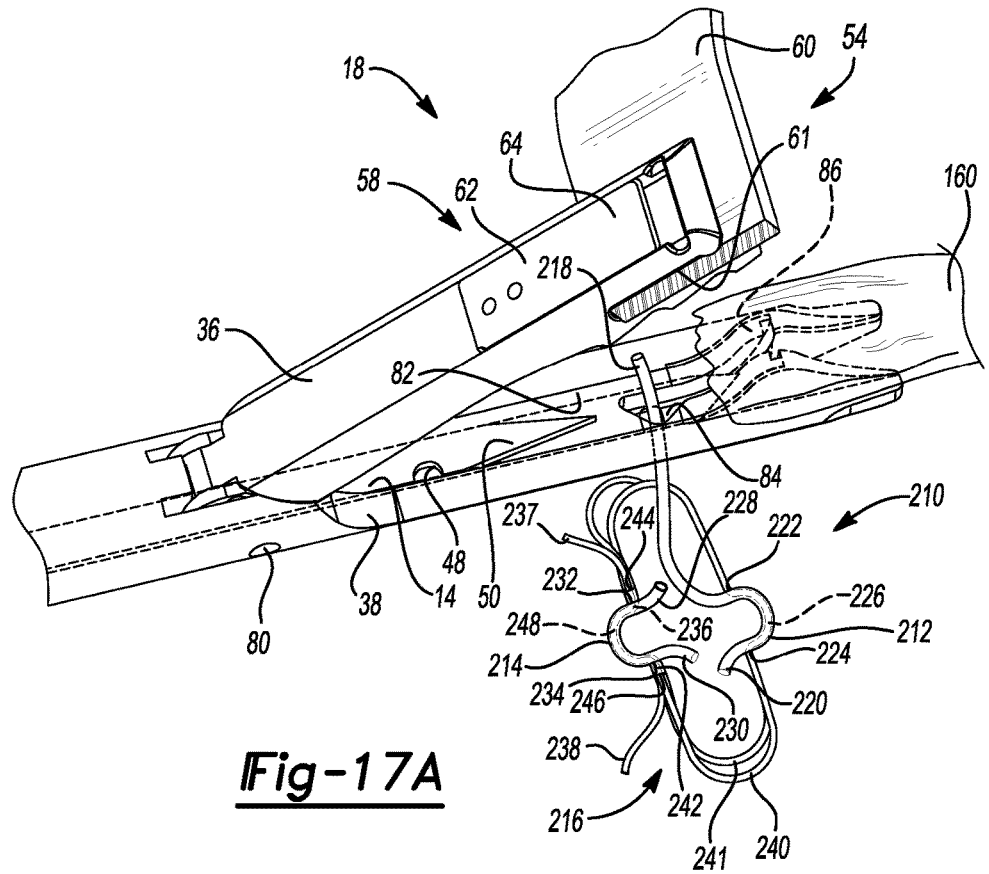
FIG. 17A is an isometric view of the suturing head with the upper jaw in the open position and positioning a tissue reinforcement construct, the suture carrier in the retracted position, and a first end of a flexible suture anchor of a suture construct extending through the lower jaw.
Figure 17B:
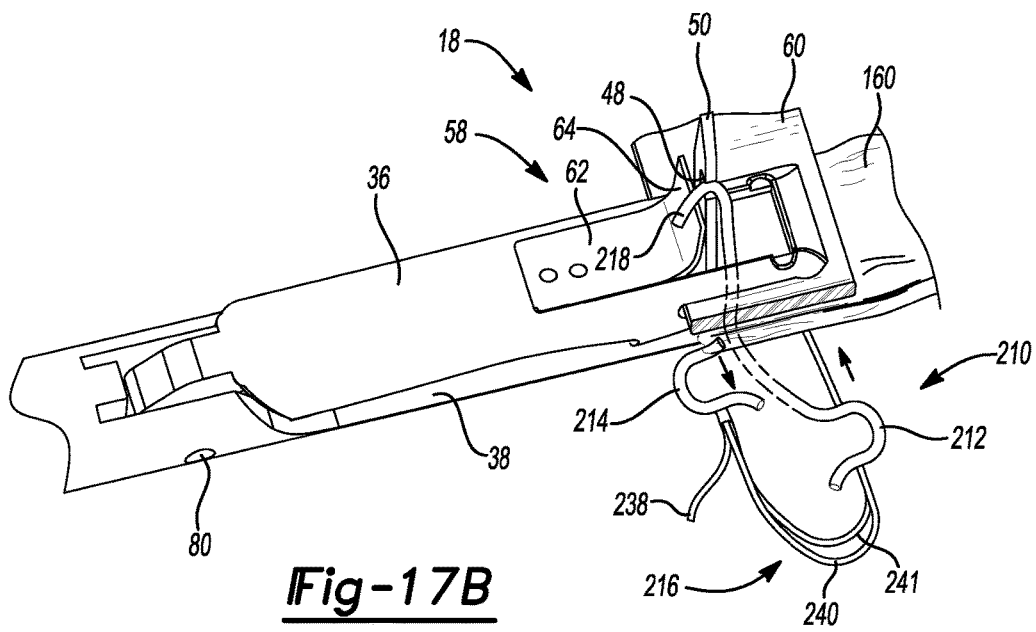
FIG. 17B is an isometric view of the suturing head in the closed position, the soft tissue being held between the upper and lower jaws, and the suture carrier in the extended position and passing the first end of the flexible suture anchor through the soft tissue and the tissue reinforcement construct.
Figure 17C:
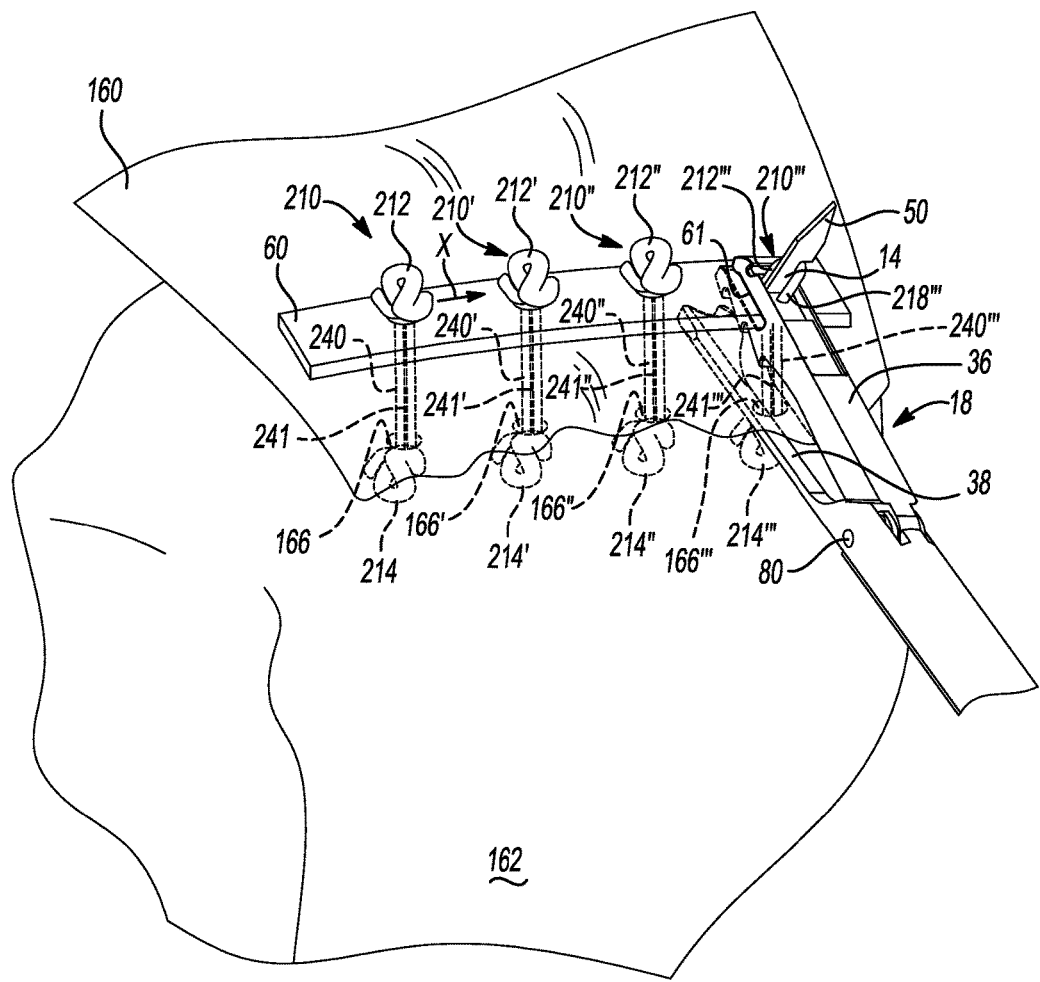
FIG. 17C is an isometric view of a plurality of suture constructs extending through soft tissue and the tissue reinforcement construct, with the suturing head passing a portion of one of the suture constructs through the soft tissue and the tissue reinforcement construct as illustrated in FIG. 17B.

Referring now to FIGS. 17A, 17B, and 17C, an example method of using the suture passer 10 and a flexible loop construct 210 to attach the soft tissue 160 to bone 162 is illustrated. The flexible loop construct 210 can include a first flexible anchor 212, a second flexible anchor 214, and a suture construct 216. Examples of flexible anchors and suture constructs are disclosed in U.S. Pat. Pub. No. 2011/0098727, the disclosure of which is incorporated herein by reference in its entirety. The flexible anchors 212, 214 may be a JuggerKnot™ Soft Anchor, available from Biomet® of Warsaw, Ind. The first flexible anchor 212 has a first end 218, a second end 220, a first opening 222, a second opening 224, and a longitudinal passage 226 extending between the first and second openings 222, 224. The first end 218 can be longer than the second end 220. The second flexible anchor 214 has a first end 228, a second end 230, a first opening 232, a second opening 234, and a longitudinal passage 236 extending between the openings 232, 234.

The suture construct 216 can include a first end 237, a second end 238, adjustable loops 240, 241, and a braided body 242. The braided body 242 can define a first opening 244, a second opening 246, and a longitudinal passage 248 extending between the first and second openings 244, 246. The first and second ends 237, 238 and the braided body 242 can be integrally formed as a single braided construct using a braiding process for braiding fibers composed of a biocompatible material. The openings 244, 246 can be created during the braiding process as loose portions between pairs of fibers. The longitudinal passage 248 can be a portion of a longitudinal passage that extends along the entire length of the suture construct 216.

To form the flexible loop construct 210, the suture construct 216 can be inserted through the longitudinal passage 236 in the second flexible anchor 214 until the braided body 242 is positioned within the longitudinal passage 236. To form the adjustable loop 240, the first end 237 of the suture construct 216 can be inserted through the longitudinal passage 226 in the first flexible anchor 212 in the direction from the first opening 222 to the second opening 224. The first end 237 can then be inserted through the longitudinal passage 248 in the braided body 242 in the direction from the second opening 246 to the first opening 244. To form the adjustable loop 241, the second end 238 of the suture construct 216 can be inserted through the longitudinal passage 226 in the first flexible anchor 212 in the direction from the second opening 224 to the first opening 222. The first end 237 can then be inserted through the longitudinal passage 248 in the braided body 242 in the direction from the first opening 244 to the second opening 246.

After the flexible loop construct 210 is formed, the first end or tail 218 of the first flexible anchor 212 can be inserted through the suture receptacle 84 in the lower jaw 38, as shown in FIG. 17A. The upper jaw 36 can then be closed, and the suture carrier 14 can be advanced using only one hand to pass the tail 218 of the first flexible anchor 212 through both the soft tissue 160 and the tissue reinforcement member 60 simultaneously, as shown in FIG. 17B. An instrument such as forceps can then be used to grab the tail 218 and pull the remainder of the first flexible anchor 212 through the soft tissue 160 and the tissue reinforcement member 60.

Before or after the first flexible anchor 212 is passed through the soft tissue 160 and the tissue reinforcement member 60, the second flexible anchor 214 can be inserted into the hole 166 in the bone 162. Tension can then be applied to the first and second ends 237, 238 of the suture construct 216 to decrease the size of the adjustable loops 240, 241 and thereby bring the soft tissue 160 closer to the bone 162. As tension in the adjustable loops 240, 241 increases, the flexible anchors 212, 214 deform as shown in FIG. 17C. This prevents the first flexible anchor 212 from being pulled through the tissue reinforcement member 60 and prevents the second flexible anchor 214 from being pulled out of the hole 166 in the bone 162.

After the suture passer 10 is used to pass the first flexible anchor 212 through the soft tissue 160 and the tissue reinforcement member 60, the suture passer 10 can be moved in a direction X without removing the member 60 from the slot 61 in the upper jaw 36. The suture passer 10 can then be used to pass first flexible anchors 212', 212", 212'" of flexible loop constructs 210', 210", 210'" through the soft tissue 160 and the tissue reinforcement member 60 in the manner described above. The bone 162 may be a humerus, and FIG. 17C may illustrate a rotator cuff repair. The suture passer 10 can also be used to repair an Achilles tendon or to attach soft tissue to soft tissue.

Figure 18A:
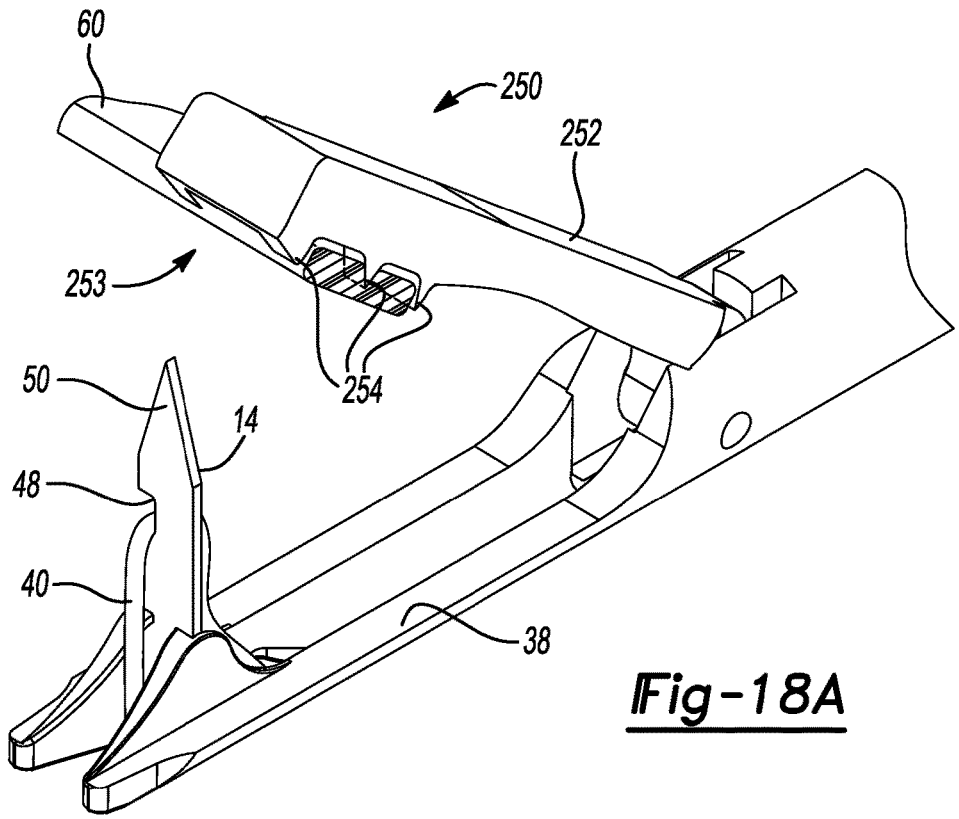
FIG. 18A is an isometric view similar to that shown in FIG. 13 but illustrating an alternative embodiment of a suturing head having teeth for positioning the tissue reinforcement construct instead of a slot.
Figure 18B:
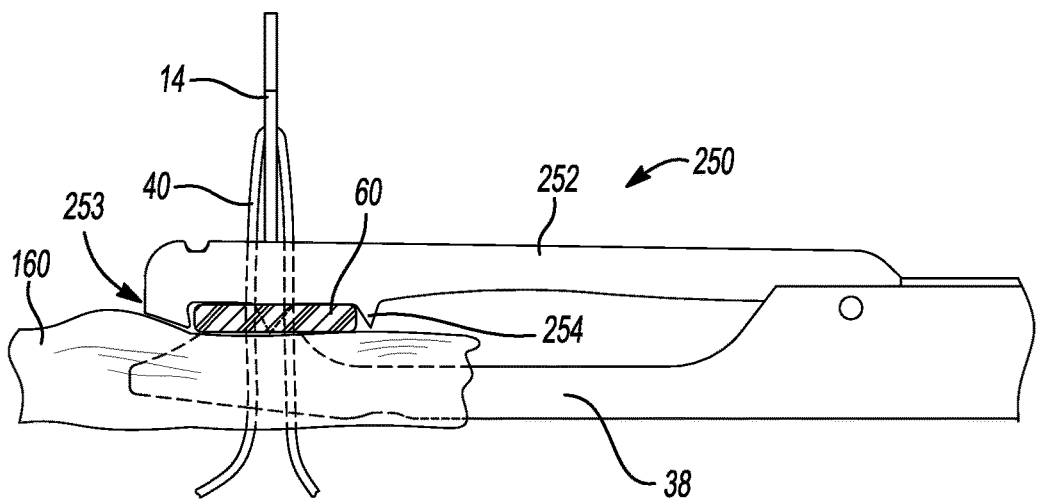
FIG. 18B is a side view similar to that shown in FIG. 14 but illustrating the alternative embodiment of the suturing head.

Referring now to FIGS. 18A and 18B, a suturing head 250 is illustrated that is similar to the suturing head 18 except that the suturing head 250 includes an upper jaw 252 instead of the upper jaw 36. The upper jaw 252 is similar to the upper jaw 36 except the upper jaw 252 includes a tissue reinforcement member holder 253 formed as teeth 254 on the underside of the upper jaw 252. The teeth 254 are configured to bite into or grip the tissue reinforcement member 60 when the tissue reinforcement member 60 is positioned on the teeth 254 as shown in FIG. 18A. Thereafter, the teeth 254 hold or retain the tissue reinforcement member 60 to fix the tissue reinforcement member 60 to the upper jaw 252. The teeth 254 can have barbed or hooked ends that enable the teeth 254 to hold the tissue reinforcement member 60. The teeth 254 can also be configured to bite into or grip the soft tissue 160 when the upper jaw 252 is closed while the soft tissue is position between the upper and lower jaws 252, 38. For example, the length of the teeth 254 can be greater than the thickness of the tissue reinforcement member 60. The teeth 254 can position or hold the tissue reinforcement member 60 in the path of the suture carrier 14 so that, when the upper jaw 252 is closed and the suture carrier 14 is advanced, the suture carrier 14 is passed through the tissue reinforcement member 60 as shown in FIG. 18B.

Figure 19A:
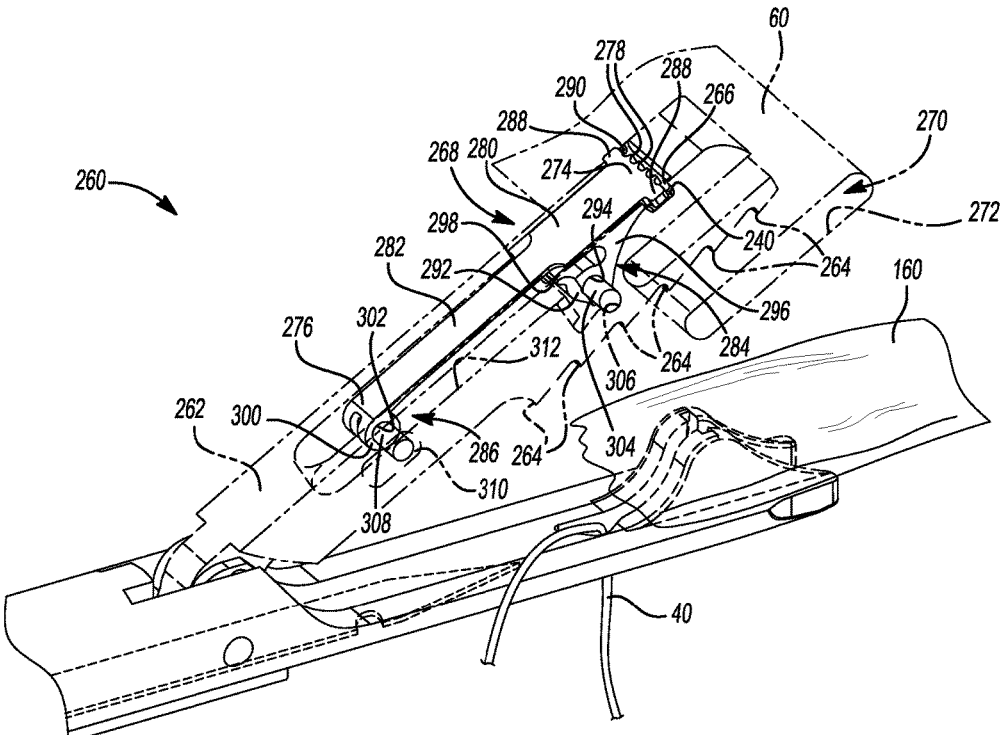
FIG. 19A is an isometric view similar to that shown in FIG. 13 but illustrating a second alternative embodiment of a suturing head for positioning the tissue reinforcement construct instead of a slot.
Figure 19B:
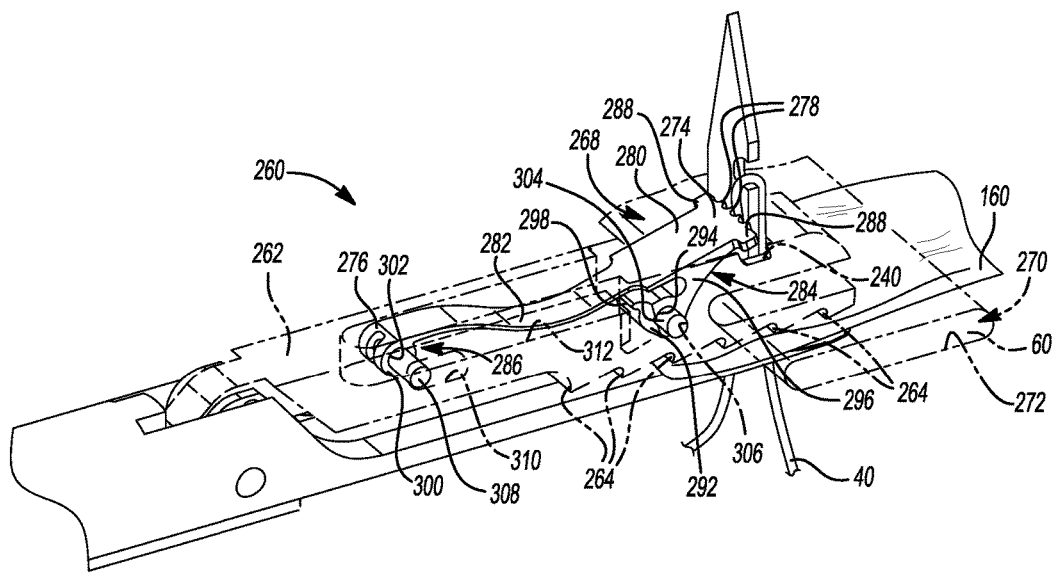
FIG. 19B is a side view similar to that shown in FIG. 14 but illustrating a second alternative embodiment of the suturing head.

Referring now to FIGS. 19A and 19B, a suturing head 260 is illustrated that is similar to the suturing head 18 except that the suturing head 250 includes an upper jaw 262 instead of the upper jaw 36. The upper jaw 262 includes teeth 264, a suture carrier receptacle 266, and a suture retaining mechanism 268. The teeth 264 are configured to bite into or grip the soft tissue 160 when the upper jaw 262 is in its closed position.

In various implementations, the upper jaw 262 can also include a tissue reinforcement member holder 270. The tissue reinforcement member holder 270 is configured to position the tissue reinforcement member 60 so that the suture carrier 14 and the suture 40 pass through the tissue reinforcement member 60 after passing through soft tissue held between the upper and lower jaws 262, 38. The tissue reinforcement member holder 270 may be a slot 272, as shown, which is similar to the slot 61 in the upper jaw 36 of the suturing head 18.

The suture carrier receptacle 266 can be an opening in the upper jaw 36. The suture carrier receptacle 266 can extend through portions of the upper jaw 262 disposed above and below the slot 272. The suture carrier 14 and the suture 40 can be passed through the suture carrier receptacle 266 after passing through soft tissue held between the upper and lower jaws 262, 38.

The suture retaining mechanism 268 prevents unintentional movement of the suture 40 out of the upper jaw 262 by maintaining the suture 40 at or near the suturing head 18. The suture retaining mechanism 268 can be made of a resilient and flexible material, such as spring steel, Nitinol, or a flexible polymer. The suture retaining mechanism 268 can include a distal end 274, a proximal end 276, teeth 278, a wide, substantially flat, rectangular body 280, a narrow, substantially flat, rectangular body 282, a first pin-receiving portion 284, and a second pin-receiving portion 286. The teeth 278 can be disposed at the distal end 274 and can be configured to engage the suture 40 to maintain the suture 40 at or near the suturing head 18.

The suture carrier 14 can be passed into the receptacle 266, temporarily disrupting the distal end 274 of the suture retaining mechanism 268 from a closed position (FIG. 19A) in contact with the upper jaw 262 to an open position (FIG. 19B) spaced apart from the upper jaw 262. The suture carrier 14 can then be retracted through the receptacle 266, allowing the distal end 274 to return to its closed position. In turn, the suture retaining mechanism 268 biases the suture 40 against the receptacle 266 to prevent the suture 40 from being pulled back through the receptacle 266. The suture retaining mechanism 268 can include ears 288 extending from the rectangular body 280 and configured to engage stops 290 on the upper jaw 262 disposed on opposite sides of the receptacle 266 as the distal end 274 returns to its closed position.

The first pin-receiving portion 284 includes a first cylindrical portion 292 defining a first pin hole 294, a neck portion 296 extending from the rectangular body 280 to the first cylindrical portion 292, and a tail 298 extending from the first cylindrical portion 292. The second pin-receiving portion 286 includes a second cylindrical portion 300 attached to the rectangular body 280 and defining a second pin hole 302. A first pin 304 can be inserted into a first pin hole 306 in the upper jaw 262 and into the first pin hole 294 in the suture retaining mechanism 268 to couple the suture retaining mechanism 268 to the upper jaw 262 adjacent to the distal end 274 of the mechanism 268. A second pin 308 can be inserted into a second pin hole 310 in the upper jaw 262 and into the second pin hole 302 in the suture retaining mechanism 268 to couple the proximal end 276 of the mechanism 268 to the upper jaw 262.

Thus, the suture retaining mechanism 268 can be coupled to the upper jaw 262 using two pin connections disposed at or near the distal and proximal ends 274, 276 of the mechanism 268. In turn, if the suture retaining mechanism 268 fractures at a location between the two pin connections, such as at the junction between the rectangular bodies 280, 282, the two portions of the suture retaining mechanism 268 on opposite sides of the fracture remain coupled to the upper jaw 262. Therefore, the design of the upper jaw 262 ensures that no portion of the suture retaining mechanism 268 is left inside of a patient in the event of a fracture.

As the distal end 274 moves from its closed position to its open position, the first pin-receiving portion 284 rotates counterclockwise about the first pin 304, the rectangular body 282 flexes downward, and the second pin-receiving portion 286 moves distally. The first pin-receiving portion 284 can rotate counterclockwise about the first pin 304 until the tail 298 on the first pin-receiving portion 284 contacts a ledge 312 on the upper jaw 262. In this regard, the ledge 312 on the upper jaw 262 can act as a stop that limits counterclockwise rotation of the first pin-receiving portion 284. Conversely, as the distal end 274 moves from its open position to its closed position, the first pin-receiving portion 284 rotates clockwise about the first pin 304, the rectangular body 282 returns to its relaxed state, and the second pin-receiving portion 286 moves proximally. The second pin hole 310 can be a slot rather than a cylindrical hole such that the second pin 308 can move distally or proximally in the second pin hole 310 to allow the distal or proximal movement of the second pin-receiving portion 286.

Figure 20A:
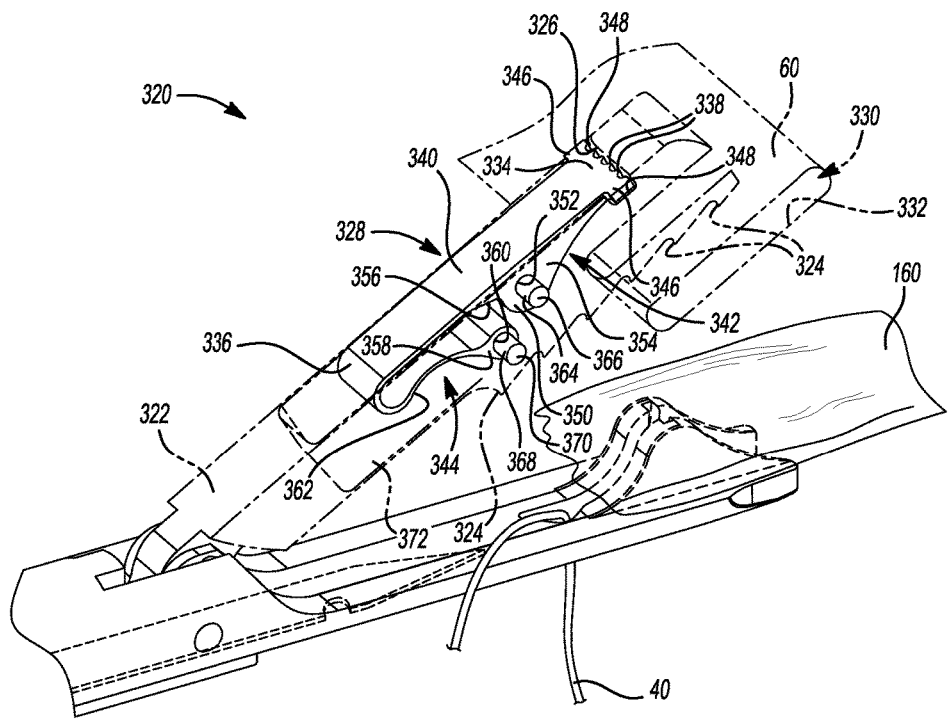
FIG. 20A is an isometric view similar to that shown in FIG. 13 but illustrating a third alternative embodiment of a suturing head having teeth for positioning the tissue reinforcement construct instead of a slot.
Figure 20B:
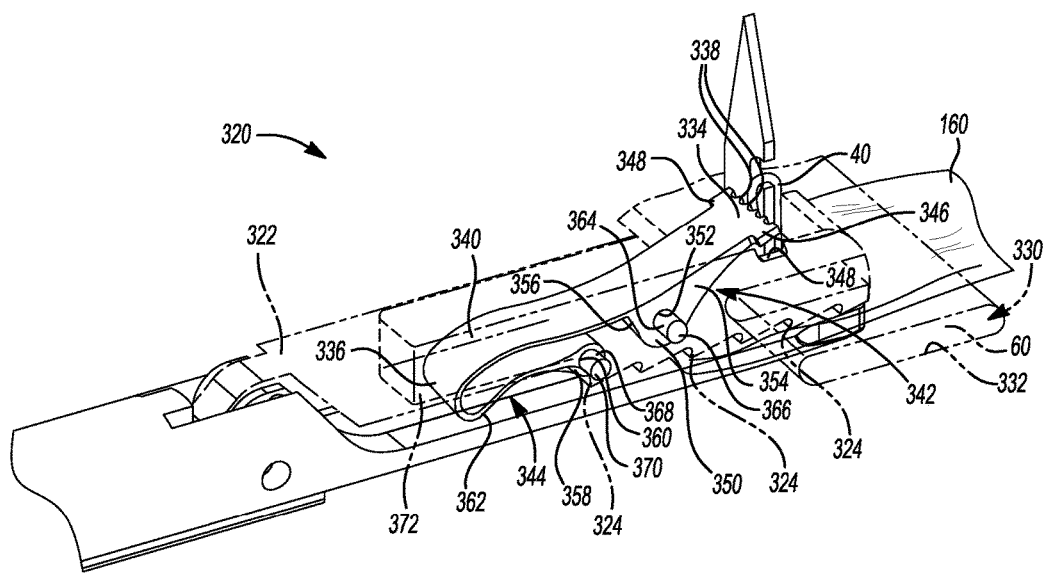
FIG. 20B is a side view similar to that shown in FIG. 14 but illustrating a third alternative embodiment of the suturing head.

Referring now to FIGS. 20A and 20B, a suturing head 320 is illustrated that is similar to the suturing head 18 except that the suturing head 320 includes an upper jaw 322 instead of the upper jaw 36. The upper jaw 322 includes teeth 324, a suture carrier receptacle 326, and a suture retaining mechanism 328. The teeth 324 are configured to bite into or grip soft tissue when the upper jaw 322 is in its closed position.

In various implementations, the upper jaw 322 can also include a tissue reinforcement member holder 330. The tissue reinforcement member holder 330 is configured to position the tissue reinforcement member 60 so that the suture carrier 14 and the suture 40 pass through the tissue reinforcement member 60 after passing through soft tissue held between the upper and lower jaws 322, 38. The tissue reinforcement member holder 330 may be a slot 332, as shown, which is similar to the slot 61 in the upper jaw 36 of the suturing head 18.

The suture carrier receptacle 326 can be an opening in the upper jaw 322. The suture carrier receptacle 326 can extend through portions of the upper jaw 262 disposed above and below the slot 332. The suture carrier 14 and the suture 40 can be passed through the suture carrier receptacle 326 after passing through soft tissue held between the upper and lower jaws 322, 38.

The suture retaining mechanism 328 prevents unintentional movement of the suture 40 out of the upper jaw 322 by maintaining the suture 40 at or near the suturing head 18. The suture retaining mechanism 268 can be made of a resilient and flexible material, such as spring steel, Nitinol, or a flexible polymer. The suture retaining mechanism 328 can include a distal end 334, a proximal end 336, teeth 338, a flat rectangular body 340, a first pin-receiving portion 342, and a second pin-receiving portion 344. The teeth 338 can be disposed at the distal end 334 and can be configured to engage the suture 40 to maintain the suture 40 at or near the suturing head 18.

The suture carrier 14 can be passed into the receptacle 326, temporarily disrupting the distal end 334 of the suture retaining mechanism 328 from a closed position (FIG. 20A) in contact with the upper jaw 322 to an open position (FIG. 19B) spaced apart from the upper jaw 322. The suture carrier 14 can then be retracted through the receptacle 326, allowing the distal end 334 to return to its closed position. In turn, the suture retaining mechanism 328 biases the suture 40 against the receptacle 326 to prevent the suture 40 from being pulled back through the receptacle 326. The suture retaining mechanism 328 can include ears 346 extending from the rectangular body 340 and configured to engage stops 348 on the upper jaw 322 disposed on opposite sides of the receptacle 326 as the distal end 334 returns to its closed position.

The first pin-receiving portion 342 includes a first cylindrical portion 350 defining a first pin hole 352, a distal fillet 354 extending between first cylindrical portion 350 and the rectangular body 340, and a proximal fillet 356 extending between first cylindrical portion 350 and the rectangular body 340. The second pin-receiving portion 344 includes a second cylindrical portion 358 defining a second pin hole 360, and a curved spring portion 362 extending from the rectangular body 340 to the second cylindrical portion 358. A first pin 364 can be inserted into a first pin hole 366 in the upper jaw 322 and into the first pin hole 352 in the suture retaining mechanism 328 to couple the mechanism 328 to the upper jaw 322 adjacent to the distal end 334 of the mechanism 328. A second pin 368 can be inserted into a second pin hole 370 in the upper jaw 322 and into the second pin hole 360 in the suture retaining mechanism 328 to couple the proximal end 336 of the mechanism 328 to the upper jaw 322.

Thus, the suture retaining mechanism 328 can be coupled to the upper jaw 322 using two pin connections. In turn, if the suture retaining mechanism 328 fractures at a location between the two pin connections, such as across the width of the spring portion 362, the two portions of the mechanism 268 on opposite sides of the fracture remain coupled to the upper jaw 322. Therefore, the design of the upper jaw 322 ensures that no portion of the suture retaining mechanism 328 is left inside of a patient in the event of a fracture.

As the distal end 334 moves from its closed position to its open position, the first pin-receiving portion 342 rotates counterclockwise about the first pin 364 and the spring portion 362 flexes downward through a bottom opening 372 in the upper jaw 322. Conversely, as the distal end 274 moves from its open position to its closed position, the first pin-receiving portion 284 rotates clockwise about the first pin 364 and the spring portion 362 returns to its relaxed state. In various implementations, the spring portion 362 may be configured to flex downward without extending through the bottom opening 372 in the upper jaw 322 to avoid contact between the spring portion 362 and the soft tissue 160. For example, the flexibility of the spring portion 362 can be adjusted by altering the geometry and/or material of the spring portion 362.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A suture passer device comprising:
    a handle;
    a shaft extending from the handle;
    a suturing head extending from the shaft and configured to engage tissue and to pass a suture through the tissue;
    a tissue reinforcement member which is separate from and discrete from the suturing head, wherein the tissue reinforcement member is configured to increase the strength of a repair by reinforcing soft tissue; and
    a tissue reinforcement member holder configured to retain the tissue reinforcement member relative to the suturing head, the tissue reinforcement member holder including a slot with open lateral sides, the slot configured to receive and hold a tissue reinforcement member in a position such that a suture carrier advances through the tissue reinforcement member, the suturing head further including a suture retaining mechanism located over the slot, the suture retaining mechanism including a flexible flap located over an opening in the suturing head, the flexible flap being biased toward the opening, wherein the flexible flap includes a proximal end coupled to the suture head and a distal end defining a suture engaging portion having a closed position such that the distal end is in contact with the suturing head and an open position such that the distal end is spaced apart from the suturing head such that a suture is sandwiched between and in contact with the distal end of the flexible flap and the suturing head.

2. The suture passer device of claim 1 wherein the suture passer device is configured to pass the suture through the tissue reinforcement member and the tissue substantially simultaneously upon retaining the tissue reinforcement member relative to the suturing head with the tissue reinforcement member holder.

3. The suture passer device of claim 1 wherein the suturing head includes a first jaw and a second jaw, and the first jaw includes the tissue reinforcement member holder.

4. The suture passer device of claim 3 wherein the tissue reinforcement member holder includes teeth disposed on the first jaw and configured to hold the tissue reinforcement member.

5. The suture passer device of claim 3 wherein the tissue reinforcement member holder includes the slot defined in the first jaw and configured to receive the tissue reinforcement member.

6. The suture passer device of claim 5 wherein the slot has an open distal end, and a closed proximal end.

7. The suture passer device of claim 5 wherein the first jaw defines a suture carrier receptacle for receiving a suture carrier, and the second jaw defines a suture carrier channel for directing the suture carrier to the suture carrier receptacle in the first jaw.

8. The suture passer device of claim 7 wherein the suture carrier receptacle extends through portions of the first jaw disposed on opposite sides of the slot defined in the first jaw.

9. A suture passer device comprising:
 a handle;
 a shaft coupled to the handle;
 a suture carrier secured to the handle and extending through the shaft;
 a tissue reinforcement member which is separate from and discrete from the suturing head, wherein the tissue reinforcement member is configured to increase the strength of a repair by reinforcing soft tissue; and
 a suturing head disposed at a distal end of the shaft, the suturing head including a first jaw and a second jaw, the handle being operable to actuate at least one of the first jaw and the second jaw to retain tissue between the first and second jaws, the handle also being operable to advance the suture carrier to pass a suture through tissue retained between the first and second jaws, at least one of the first jaw and the second jaw including a tissue reinforcement member holder for holding the reinforcement member such that the suture carrier passes through the tissue reinforcement member as the suture carrier is advanced through the suturing head, the tissue reinforcement member holder including a slot with open lateral sides, the slot configured to receive and hold a tissue reinforcement member in a position such that the suture carrier advances through the tissue reinforcement member, the suturing head further including a suture retaining mechanism located over the slot, the suture retaining mechanism including a flexible flap located over an opening in the suturing head, the flexible flap being biased toward the opening, wherein the flexible flap includes a proximal end coupled to the suture head and a distal end defining a suture engaging portion having a closed position such that the distal end is in contact with the suturing head and an open position such that the distal end is spaced apart from the suturing head such that a suture is sandwiched between and in contact with the distal end of the flexible flap and the suturing head.

10. The suture passer device of claim 9 wherein the tissue reinforcement member holder includes teeth disposed on the first jaw and configured to grip the tissue reinforcement member.

11. The suture passer device of claim 9 wherein the tissue reinforcement member holder includes the slot defined in the first jaw and configured to retain the tissue reinforcement member.

12. The suture passer device of claim 11 wherein the first jaw includes teeth configured to retain tissue when the tissue is positioned between the first jaw and the second jaw and the one of the first jaw and the second jaw is actuated toward the other one of the first jaw and the second jaw.

* * * * *